US009072859B2

(12) United States Patent
Ishikita

(10) Patent No.: US 9,072,859 B2
(45) Date of Patent: Jul. 7, 2015

(54) ANESTHETIC INHALATION AID DEVICE AND ATTACHMENT USED FOR THE SAME

(76) Inventor: Naoyuki Ishikita, Iwate (JP)

( * ) Notice: Subject to any disclaimer, the term of this patent is extended or adjusted under 35 U.S.C. 154(b) by 346 days.

(21) Appl. No.: 13/812,279

(22) PCT Filed: May 31, 2012

(86) PCT No.: PCT/JP2012/064069
§ 371 (c)(1),
(2), (4) Date: Jan. 25, 2013

(87) PCT Pub. No.: WO2012/165541
PCT Pub. Date: Dec. 6, 2012

(65) Prior Publication Data
US 2013/0118484 A1 May 16, 2013

(30) Foreign Application Priority Data
May 31, 2011 (JP) ................................. 2011-122801

(51) Int. Cl.
*A61M 16/00* (2006.01)
*A61M 16/01* (2006.01)
(Continued)

(52) U.S. Cl.
CPC .............. *A61M 16/104* (2013.01); *A61M 16/01* (2013.01); *A61M 16/18* (2013.01); *A61M 11/02* (2013.01);
(Continued)

(58) Field of Classification Search
CPC .............. A61M 16/10; A61M 16/104; A61M 16/0009; A61M 16/20; A61M 16/209; A61M 16/208; A61M 16/009; A61M 16/06; A61M 16/08; A61M 16/0081; A61M 16/107; A61M 16/01; A61M 16/22; A61M 11/02; A61M 16/0078; A61M 16/0816; A61M 16/0093; A61M 16/18; A62B 19/00; A62B 7/10; A62B 23/02; F16L 55/04; B01D 53/02

USPC ............ 128/205.12, 205.17, 205.28, 205.15, 128/205.13, 202.23, 204.25, 203.28, 128/203.12, 205.24, 910, 202.22, 203.16, 128/204.21, 200.14, 203.26, DIG. 26
See application file for complete search history.

(56) References Cited

U.S. PATENT DOCUMENTS 3,467,092 A * 9/1969 Bird et al. ................. 128/204.25
3,814,091 A * 6/1974 Henkin ..................... 128/202.22
(Continued)

FOREIGN PATENT DOCUMENTS

DE 2213764 A1 9/1973
DE 2231188 A1 1/1974
(Continued)

OTHER PUBLICATIONS

Supplementary European Search Report for European Patent App. No. 12791955.3 (Nov. 3, 2014).
(Continued)

*Primary Examiner* — Annette Dixon
(74) *Attorney, Agent, or Firm* — Cermak Nakajima & McGowan LLP; Tomoko Nakajima

(57) ABSTRACT

An inhalation mask, an artificial nose unit, an anesthetic gas concentration detector, an extension tube, an anesthesia attachment, and an elastic bag are in communicative connection in sequence. The elastic bag has a mixing chamber formed therein and has an anesthetic inlet, an air inlet, and an outlet port each formed at the boundary to the exterior. The anesthesia attachment includes a hollow structure and an evaporation injector syringe. The outlet port of the elastic bag is in communicative connection with the hollow structure through its opening, and the evaporation injector syringe tightly mates with the interior of another opening. The anesthetic introduced into the mixing chamber is vaporized and then mixed with air introduced from the air inlet into mixed gas. The mixed gas is supplied from the outlet port to the inhalation mask by compressing the elastic bag or other procedures.

21 Claims, 17 Drawing Sheets

(51) Int. Cl.
*A61M 16/18* (2006.01)
*A61M 16/08* (2006.01)
*A61M 16/22* (2006.01)
*A61M 16/20* (2006.01)
*A61M 16/10* (2006.01)
*A61M 11/02* (2006.01)
*A61M 11/06* (2006.01)
*A61M 11/00* (2006.01)
*A61M 11/04* (2006.01)
*A61M 15/00* (2006.01)

(52) U.S. Cl.
CPC ........... *A61M 11/06* (2013.01); *A61M 16/0078* (2013.01); *A61M 16/0816* (2013.01); *A61M 16/1045* (2013.01); *A61M 16/208* (2013.01); *A61M 2016/1035* (2013.01); *A61M 2205/071* (2013.01); *A61M 2205/075* (2013.01); *A61M 2205/3653* (2013.01); *A61M 2205/502* (2013.01); *A61M 2205/505* (2013.01); *A61M 2205/6045* (2013.01); *A61M 2205/6081* (2013.01); *A61M 2205/8206* (2013.01); *A61M 2230/04* (2013.01); *A61M 2230/205* (2013.01); *A61M 2230/30* (2013.01); *A61M 2230/437* (2013.01); *A61M 11/006* (2014.02); *A61M 11/007* (2014.02); *A61M 11/042* (2014.02); *A61M 15/002* (2014.02); *A61M 16/0093* (2014.02); *A61M 16/209* (2014.02)

(56) References Cited

U.S. PATENT DOCUMENTS

| 3,901,230 | A | * | 8/1975 | Henkin | 128/205.17 |
| 4,051,847 | A | * | 10/1977 | Henkin | 128/202.22 |
| 5,592,934 | A | | 1/1997 | Thwaites | |
| 5,803,064 | A | | 9/1998 | Phelps et al. | |
| 6,067,984 | A | | 5/2000 | Piper | |
| 6,253,767 | B1 | * | 7/2001 | Mantz | 128/205.13 |
| 6,275,650 | B1 | | 8/2001 | Lambert | |
| 2009/0151720 | A1 | | 6/2009 | Inoue et al. | |
| 2010/0132706 | A1 | | 6/2010 | Nashed | |
| 2010/0192947 | A1 | | 8/2010 | Mandel et al. | |

FOREIGN PATENT DOCUMENTS

| EP | 0467362 A1 | 1/1992 |
| EP | 0504977 A1 | 9/1992 |
| JP | 52-94692 A | 8/1977 |
| JP | 5-84302 A | 4/1993 |
| JP | 6-319802 A | 11/1994 |
| JP | 2001-095921 A | 4/2001 |
| JP | 2001-519699 A | 10/2001 |
| JP | 2002-529155 A | 9/2002 |
| WO | WO90/02577 A1 | 3/1990 |
| WO | WO00/27458 A1 | 5/2000 |
| WO | WO2007/129515 A1 | 11/2007 |

OTHER PUBLICATIONS

International Search Report for PCT Patent App. No. PCT/JP2012/064069 (Jun. 26, 2012).

* cited by examiner (A)

(B)

ANESTHETIC INHALATION AID DEVICE AND ATTACHMENT USED FOR THE SAME

TECHNICAL FIELD

The present invention relates to an anesthetic inhalation aid device for administrating an anesthetic to a patient by inhalation, in particular, relates to an anesthetic inhalation aid device which can be easily handled and enables prompt inhalation administration of an anesthetic to a patient and an attachment used therefor.

BACKGROUND ART

A convulsive seizure induced by recurrent excessive firing of brain neurons is known to be attributed to various causes including not only central nervous system diseases, such as epilepsy and stroke, but also infections, such as encephalitis and meningitis, head injuries, acute alcoholism, and acute drug intoxication. In particular, if status epilepticus in which firing throughout the cerebral cortex lasts for several tens of minutes or longer from the start of the seizure occurs, an imbalance between metabolic and bloodstream is caused, which may lead to irreversible brain damage. Even if hypoxemia, hypoglycemia, or local circulatory disorder is not caused, the excessive neuroelectronic activity itself causes brain damage. Status epilepticus is therefore known to cause severe mental or neurological aftereffects due to this irreversible brain damage. Within a certain period of time after status epilepticus occurs, brain damage is less likely to be caused owing to a compensatory action; however, if treatment takes time, compensation becomes impossible, and severe brain damage is therefore likely to be developed. This evokes a need for treatment which terminates convulsions as soon as possible after the start of a seizure while an airway is promptly maintained.

The method most widely used for convulsive treatment is administration of a medicine by an intravenous injection or intramuscular injection which have an immediate effect. It is, however, difficult to safely give the injection to a patient being in a convulsive state. In addition, if a medicine is excessively administered, it is difficult to remove the medicine from the body, which causes the risk of unstable cardiorespiratory functions. Although attempts at easier methods have been also made, such as administration of a suppository and enema administration of an intravenous medicine, these methods have unsatisfactory immediate effects and are therefore unlikely to terminate convulsions at an early stage.

In contrast, there are medical findings that general anesthesia with inhalational anesthetics is the most effective for controlling status epilepticus and also has less serious side effects than other medications. In the findings, inhalational anesthetics can contribute to safe and steady administration of a medication to a patient being in a convulsive state to terminate the convulsion. Moreover, since the inhalational anesthetics are absorbed and eliminated through the lungs, the depth of anesthesia can be adjusted, which suggests that inhalational anesthetics are safer than other medications.

It is known that the administration of inhalational anesthetics involves use of a complicated inhalational anesthesia system including an anesthesia apparatus for generating mixed gas of carrier gas, such as oxygen supplied from a carrier gas source, and a volatile anesthetic to be vaporized with a vaporizer; a circular breathing circuit having a respirator for mixing the mixed gas generated by the anesthesia apparatus with the expired air of a patient and then transporting the resulting gas as intake gas of the patient; and a control unit having a computer for controlling these components (e.g., see Patent Literature 1).

CITATION LIST

Patent Literature

Patent Literature 1: Japanese Unexamined Patent Application Publication No. 2001-095921

DISCLOSURE OF THE INVENTION

Problems to be Solved by the Invention

However, in order to operate this inhalational anesthesia system, each system component needs to not only be assembled and set up but also be handled for appropriately adjusting the composition of the mixed gas generated by the anesthesia apparatus and the respiratory state created by the circular breathing circuit depending on the patient's conditions. Thus, the handling of such an inhalational anesthesia system requires high levels of technical skills as well as extensive knowledge, and only professionals of anesthesia, such as anesthesiologists, can handle the system.

Although some of inhalational anesthesia apparatuses for small animals are relatively easy to handle, such anesthesia apparatuses are used to induce anesthesia in a situation not suitable for humans, such as placing a small animal in a box filled with anesthetic gas; hence, such anesthesia apparatuses are inadequate for appropriate anesthetic management for humans.

Hence, in the case where an inhalational anesthetic is administered to a patient, the patient must be transported to a medical institution or the like where a specialist of anesthesia works. This inhibits prompt administration of an inhalational anesthetic, which causes possible fear that convulsions cannot be terminated at an early stage from the start of a convulsive seizure.

In view of the typical problems described above, the present invention has an object of providing an anesthetic inhalation aid device which can be easily handled and enables prompt inhalation administration of an anesthetic to a patient.

Means for Solving the Problems

In order to accomplish the object described above, the anesthetic inhalation aid device of the present invention is used for inhalation administration of an anesthetic in a reservoir to a patient and includes a connector that can be detachably and airtightly connected to an anesthetic outlet of the reservoir; an anesthetic extraction unit connected to the connector, being in communication with the interior of the reservoir, and including an anesthetic extraction channel for unidirectionally introducing the anesthetic from the interior of the reservoir to the exterior; a mixer having an anesthetic inlet for introducing the anesthetic inward through the anesthetic extraction channel, an oxygen-containing gas inlet for unidirectionally introducing oxygen-containing gas at least containing oxygen from the exterior to the interior, a mixing chamber for mixing the introduced anesthetic with the oxygen-containing gas, and an outlet port for exhausting the mixed gas generated in the mixing chamber outward from the mixing chamber, the anesthetic inlet being formed so as to extend from the outlet port to the mixing chamber; a mixed gas introduction passage for unidirectionally introducing the mixed gas from the outlet port to the oral cavity or nasal cavity of the patient; a relief valve that opens when the internal pressure of the mixed gas introduction passage reaches a level greater than or equal to a first predetermined pressure; and a remover that removes an anesthetic content in gas exhausted from the relief valve. The mixer is configured as an elastic bag that is elastically deformed by hand to increase and decrease the volume of the mixing chamber, the mixed gas is exhausted from the outlet port when the volume is decreased, and the oxygen-containing gas is introduced from the oxygen-containing gas inlet when the volume is increased.

Effect of the Invention

The anesthetic inhalation aid device of the present invention can be easily handled and enables prompt inhalation administration of an anesthetic to a patient.

DESCRIPTION OF EMBODIMENTS

Embodiments of the present invention will be described in detail with reference to the accompanying drawings.

Figure 1:
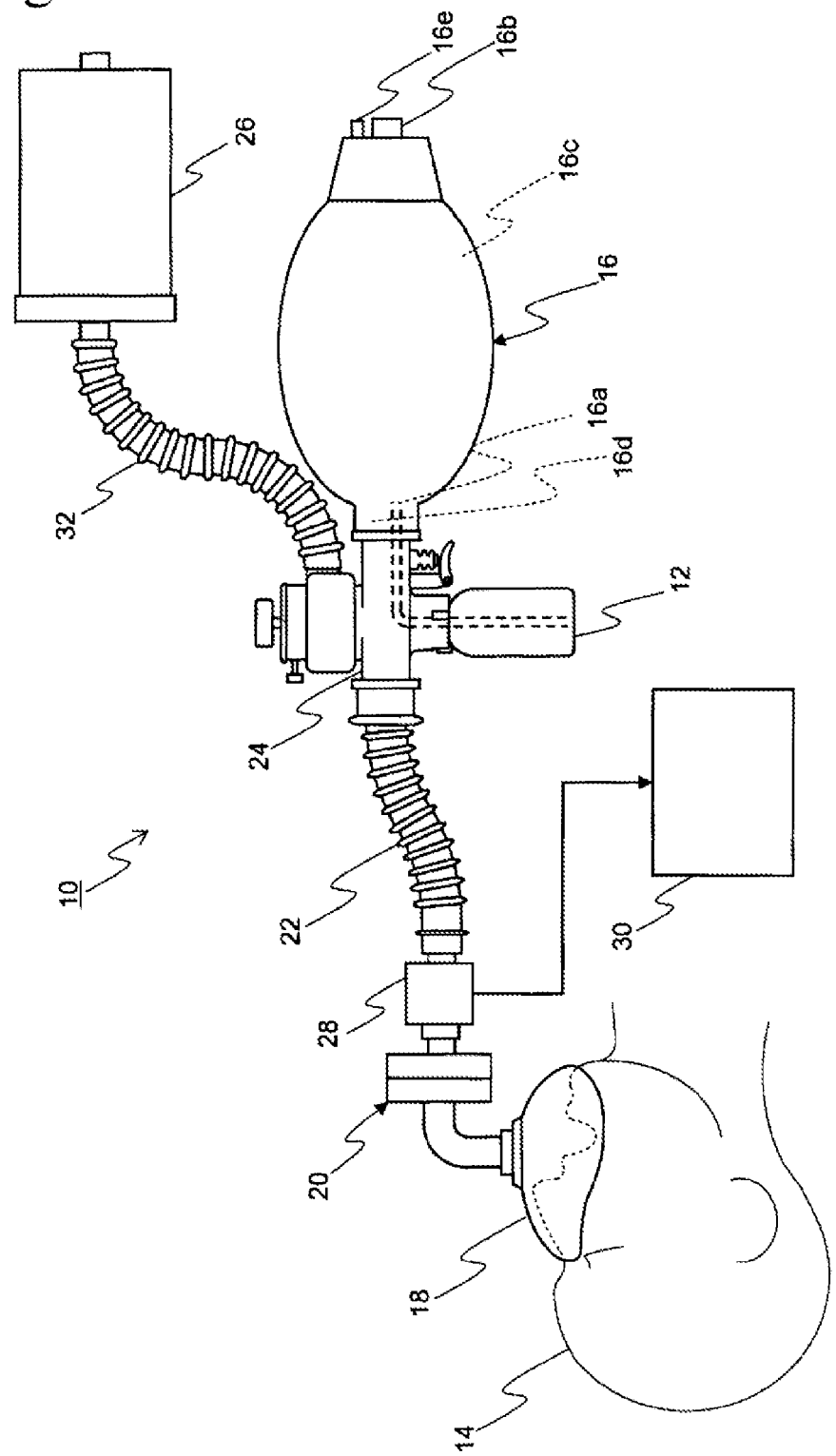
FIG. 1 is a general view illustrating an example of an anesthetic inhalation aid device according to a first embodiment of the present invention.

FIG. 1 illustrates an example of an anesthetic inhalation aid device according to a first embodiment. An anesthetic inhalation aid device 10 enables inhalation administration of an anesthetic to a patient 14, the anesthetic being supplied from an anesthetic bottle 12 being a reservoir of the anesthetic. The anesthetic inhalation aid device 10 includes an elastic bag 16, an inhalation mask 18, an artificial nose unit 20, an extension tube 22, an anesthesia attachment 24, anesthetic removal equipment 26, an anesthetic gas concentration detector 28, a display 30, and an exhaust tube 32.

The elastic bag 16 functions as a mixer and has an anesthetic inlet 16a for introducing an anesthetic held by the anesthetic bottle 12 to the interior through the anesthesia attachment 24 which will be described in detail later, an air inlet 16b with a backflow prevention function for unidirectionally introducing air to the interior, a mixing chamber 16c for mixing the introduced anesthetic with the introduced air into mixed gas, and an outlet port 16d for discharging the mixed gas to the exterior. Since the elastic bag 16 is composed of an elastic material such as silicone, the mixing chamber 16c can be elastically deformed by hand to change the volume thereof. The mixed gas is transported from the outlet port 16d by application of pressure when the volume of the mixing chamber 16c is decreased, and air is introduced from the air inlet 16b when the mixing chamber 16c returns to the original volume state. The transportation of the mixed gas by application of pressure and the introduction of air can be carried out not only by the forced ventilation through compression and expansion of the elastic bag 16 but also by voluntary respiration of the patient 14. An oxygen reservoir (not illustrated) in which oxygen gas is reserved may be connected to the air inlet 16b of the elastic bag 16 to enhance oxygen concentration in the mixed gas; in place of, or in addition to, the oxygen reservoir, a pressure container in which oxygen or air is reserved, such as ULTRESSA (registered trademark) manufactured by Teijin Engineering Limited, may be connected to a spare inlet 16e to supply oxygen gas or air from the pressure container to the mixing chamber 16c. In particular, the air inlet 16b and the spare inlet 16e function as an oxygen-containing gas inlet for unidirectionally introducing oxygen gas or air from the exterior into the interior.

The inhalation mask 18 has a dome shape so as to cover the oral cavity or nasal cavity of the patient 14 and is connected to the artificial nose unit 20. The artificial nose unit 20 has an artificial nose filter (not illustrated) inserted thereinto, and the artificial nose filter holds heat and moisture derived from the expired air of the patient 14 which pass through the nose filter, so that the inspired air of the patient 14 is warmed and moisturized. The artificial nose unit 20 may be connected to a tracheal tube or a laryngeal mask (each not illustrated) in place of the inhalation mask 18, and the same holds for the below description.

An end of the extension tube 22 is connected to the artificial nose unit 20 at the opposite side of the inhalation mask 18 relative to the artificial nose filter with the anesthetic gas concentration detector 28, which will be described in detail later, interposed therebetween. The other end of the extension tube 22 is connected to the elastic bag 16 with the anesthesia attachment 24, which will be described in detail later, interposed therebetween to increase the distance between the artificial nose unit 20 and the elastic bag 16, which can enhance the degree of freedom of operation of the anesthetic inhalation aid device 10. The extension tube 22 is, for example, formed from a flexible material in the shape of a bellows so as to have flexibility. Although the mixed gas can be directly introduced from an end of the extension tube 22 to the oral cavity or nasal cavity of the patient 14, the artificial nose unit 20 is preferably provided between the extension tube 22 and the oral cavity or nasal cavity of the patient 14 as described above in terms of prevention of infectious diseases.

The elastic bag 16, the inhalation mask 18, the artificial nose unit 20, and the extension tube 22 described above are used as standard components constituting existing manual artificial respirators (emergency manual artificial respirators or emergency manual resuscitators), and each component may have the connection form, performance, and the like which meet international standards or the likes.

The anesthetic inhalation aid device 10 is provided with the anesthesia attachment 24 which is removably connected to the outlet port 16d of the elastic bag 16 and the other end of the extension tube 22. That is, the anesthetic inhalation aid device 10 has a configuration provided by modifying the typical manual artificial respirators, in which the removable anesthesia attachment 24 is provided between the elastic bag 16 and the extension tube 22.

The anesthetic removal equipment 26 is connected to the anesthesia attachment 24 via the exhaust tube 32, removes residual anesthesia in gas discharged from the anesthesia attachment 24 by, for instance, adsorption on activated carbon, and then discharges the removed anesthesia to the atmosphere (e.g., excess anesthetic gas recovery canister "F/AIR canister" manufactured by AS ONE Corporation).

With reference to FIGS. 2 to 5, the anesthesia attachment 24 includes a hollow structure 34 having three openings of a first opening 34a, a second opening 34b, and a third opening 34c; a connector 36; a relief valve 38 utilizing the first opening 34a of the hollow structure 34 as an inlet of the valve; a sleeve 40; an exhaust chamber 42 connected to the anesthetic removal equipment 26 through the exhaust tube 32; and an anesthetic extraction unit 44.

Figure 2:
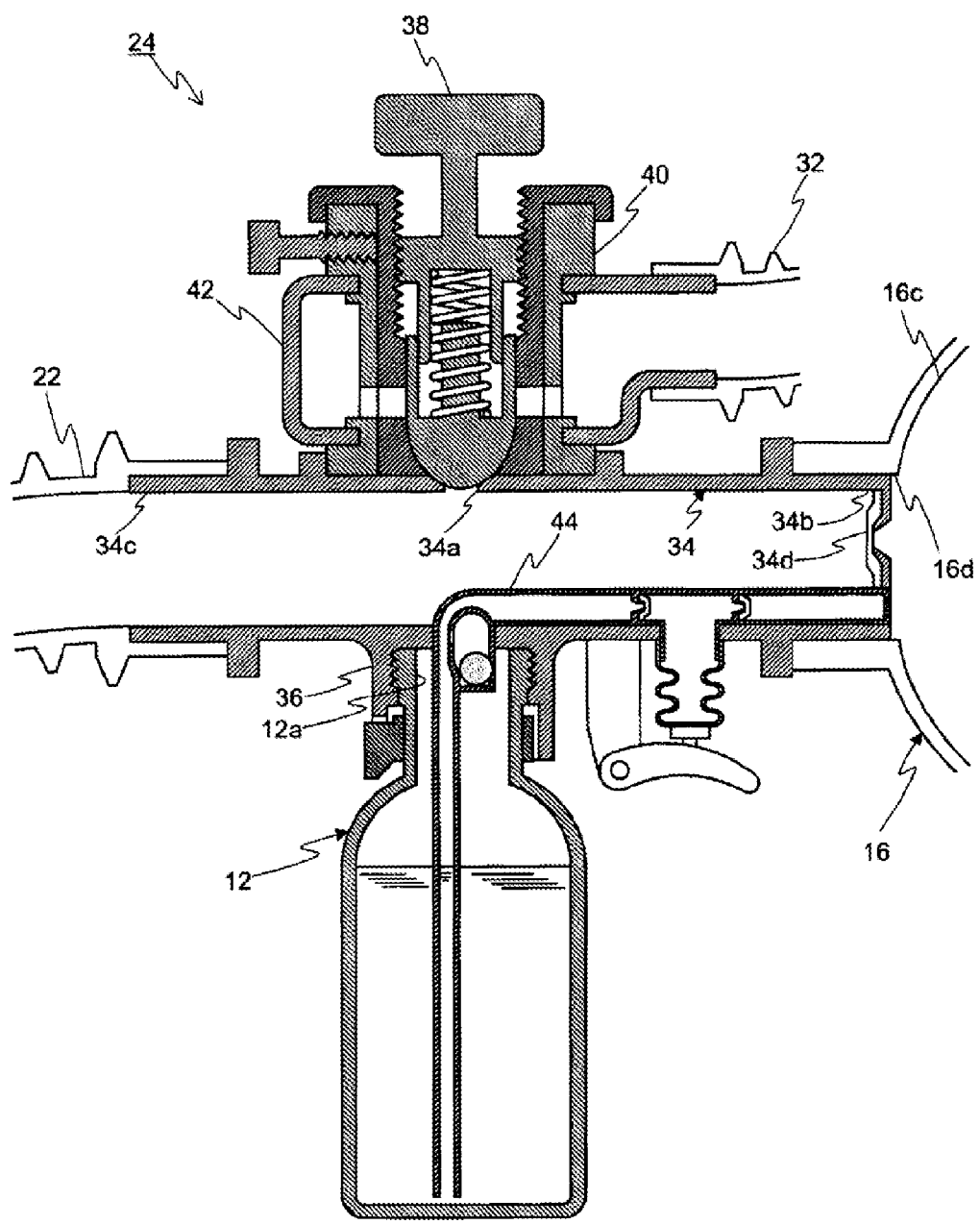
FIG. 2 is a partial cross-sectional view illustrating an anesthesia attachment.

With reference to FIG. 2, the hollow structure 34 is, for instance, in the form of a tube, is in communicative connection with the mixing chamber 16c through the outlet port 16d of the elastic bag 16 at the second opening 34b, and is in communicative connection with the extension tube 22 through the third opening 34c. A mixed gas inlet valve 34d is provided inside the hollow structure 34 at a side of the elastic bag 16 relative to the first opening 34a and allows the unidirectional flow of the mixed gas from the outlet port 16d to the extension tube 22. The mixed gas inlet valve 34d is configured by disposing a rubber on-off valve on the extension tube 22 side of a through-hole narrowing the channel of the hollow structure 34. In the mixed gas inlet valve 34d, the mixed gas output from the elastic bag 16 through the through-hole can separate the on-off vale from the through-hole owing to its pressure and then smoothly pass, while the on-off valve tightly attached to the through-hole excludes entrance of gas flowing from the extension tube 22 to the elastic bag 16 even if the gas is pressurized. The inhalation mask 18, the artificial nose unit 20, the extension tube 22, the hollow structure 34 of the anesthesia attachment 24, and the mixed gas inlet valve 34d (in addition, the anesthetic gas concentration detector 28 which will be described later) constitute a mixed gas introduction passage for unidirectionally introducing the mixed gas inside the elastic bag 16 from the outlet port 16d into at least one of the oral cavity and nasal cavity of the patient 14.

Figure 3:
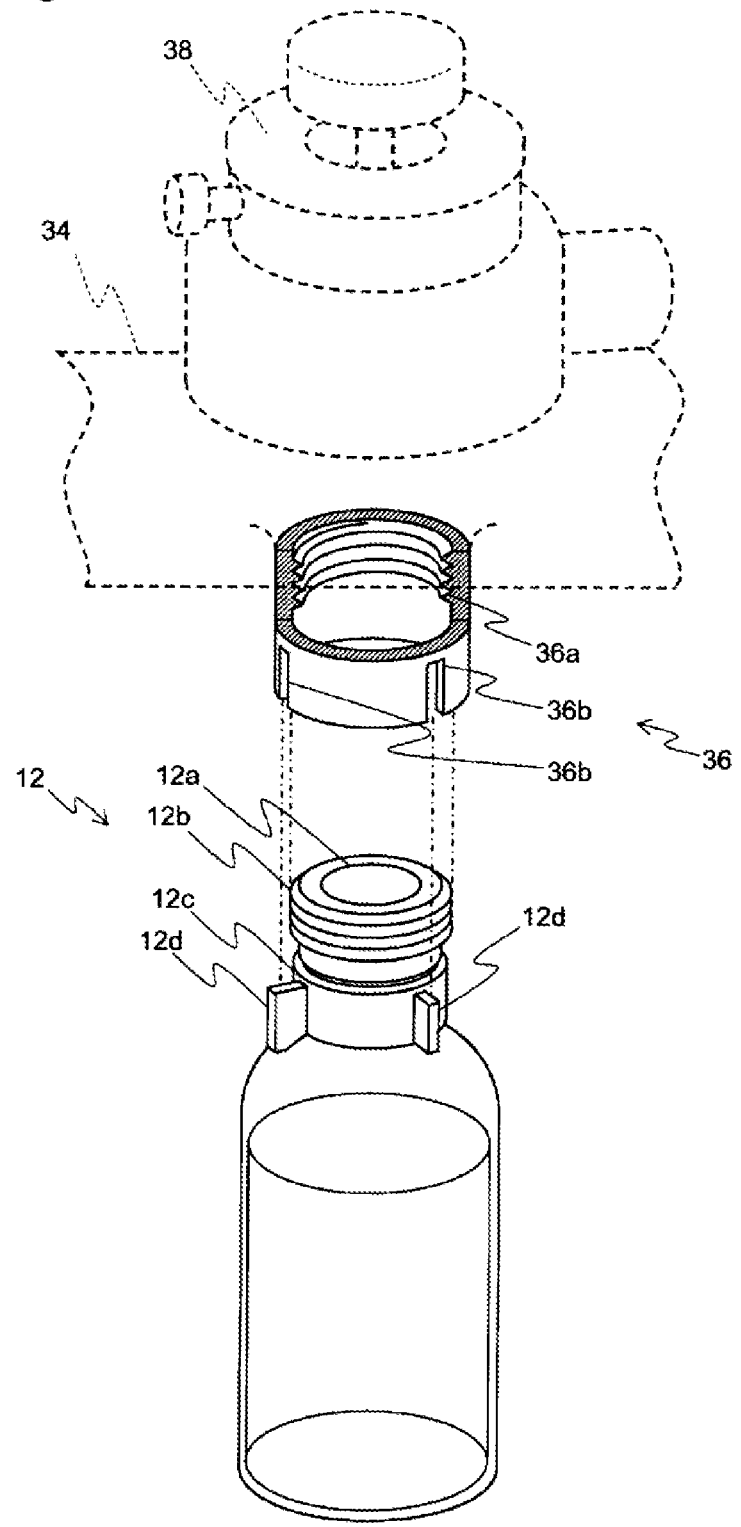
FIG. 3 is a perspective view illustrating connection of an anesthetic bottle and the anesthesia attachment.
Figure 4:
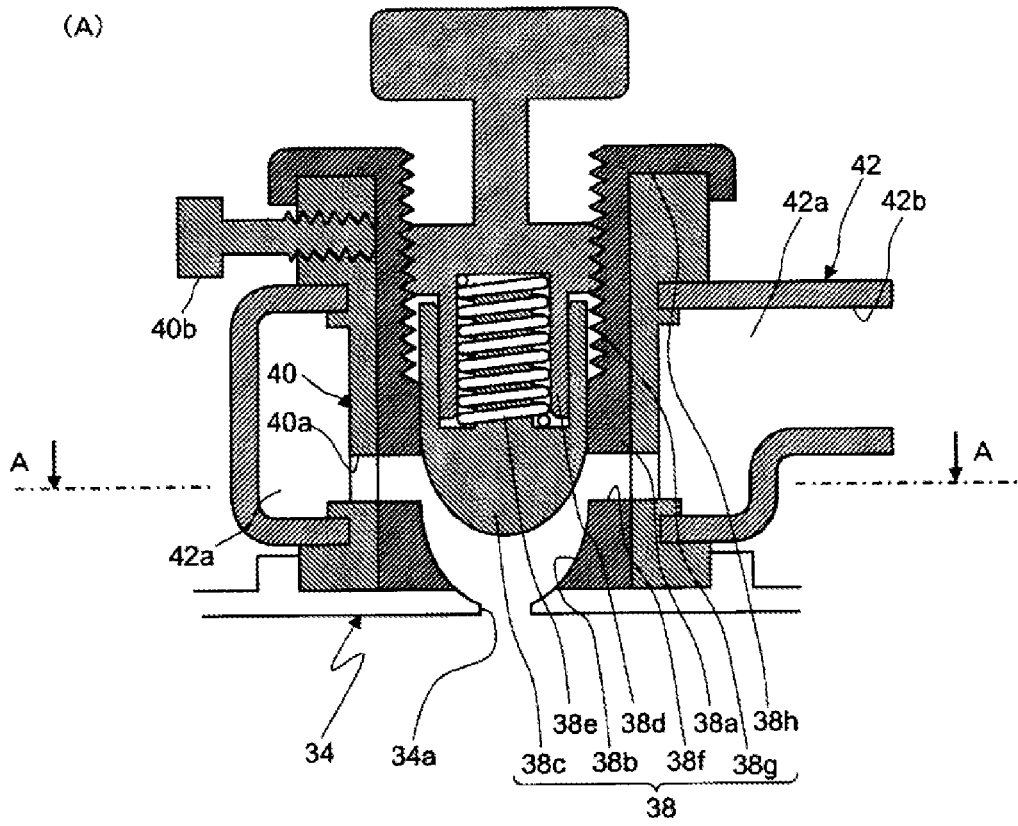
FIG. 4(A) is a partial cross-sectional view illustrating the detail of an exhaust mechanism of a relief valve in an opened state.
FIG. 4(B) is a cross-sectional view illustrating the same taken along the line A-A in FIG. 4(A).
Figure 4:
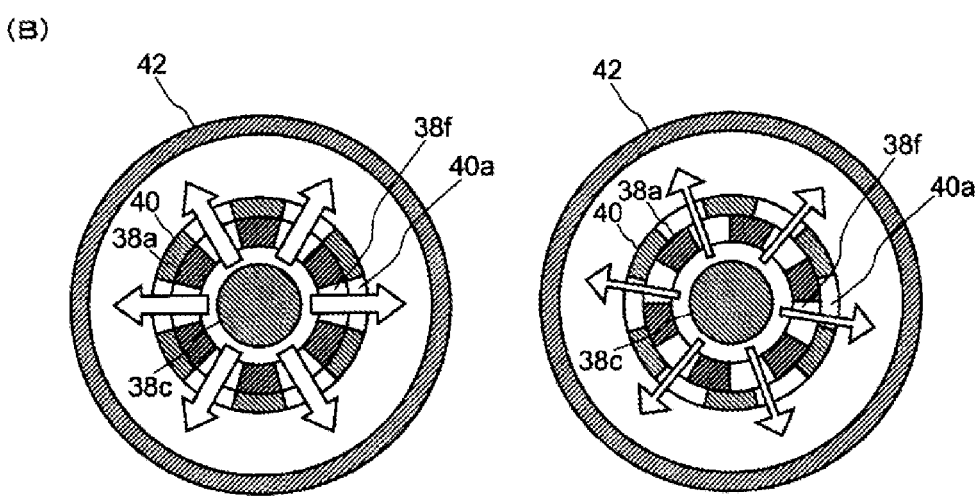

The connector 36 is provided so as to be integrated with the hollow structure 34 in the form of a bottomed cylinder which extends from the hollow structure 34 and has an opening toward the exterior, and functions as a connection device which can be detachably and airtightly attached to an anesthetic outlet 12a of the anesthetic bottle 12. With reference to FIG. 3 in detail, the inner surface of the connector 36 has a thread groove 36a which threadably mates with a screw thread 12b provided to the anesthetic outlet 12a in parallel with the circumference of the anesthetic bottle 12. The connector 36 may have any other structure provided that the connector 36 is detachably attached to the anesthetic outlet 12a of the anesthetic bottle 12. For example, a hook (not illustrated) may be provided on the inner surface of the bottomed cylinder described above to elastically mate with the screw thread 12b, which enables one-touch attachment of the anesthetic bottle 12 to the anesthesia attachment 24.

The connector 36 has slits 36b formed so as to extend from its opening end toward the interior of the hollow structure 34. The slits 36 are formed such that multiple protrusions 12d are inserted into the slits 36 before the screw thread 12b threadably mates with the thread groove 36a when the anesthetic bottle 12 is connected to the connector 36, the protrusions 12d protruding from a ring collar 12c to the outside in a radial direction, the ring collar 12c being rotatably attached to the neck of the anesthetic bottle 12. The shape of each protrusion 12d and the distance between the protrusions 12d vary depending on the type of an anesthetic in the anesthetic bottle 12, and the connector 36 can be therefore attached only to the anesthetic bottle 12 having the color 12c corresponding to a specific anesthetic. An attempt to attach the connector 36 to the anesthetic bottle 12 having the collar 12c not corresponding to a specific anesthetic prevents the insertion of the protrusions 12d into the slits 36b, and the screw thread 12b does not threadably mate with the thread groove 36a. This can prevent the connector 36 from being attached to the anesthetic bottle 12 having the collar 12c not corresponding to a specific anesthetic, which eliminates wrong administration of the anesthetic. It is preferred that the connector 36 be provided so as to be removable from the anesthesia attachment 24 and that multiple types of connector 36 be prepared depending on the shapes of the protrusions 12d and different types of collar 12c having different distances between the protrusions 12d. Such a structure enables the anesthesia attachment 24 to be connected to an anesthetic bottle 12 adequate for the purpose of inhalation anesthesia which is selected from different types of anesthetic bottles 12 holding different anesthetics, respectively.

The anesthetic bottle 12 selectively contains a volatile anesthetic suitable for inhalational anesthetic, such as sevoflurane or isoflurane, depending on the intended use. Bottles containing a commercially available anesthetic [e.g., 250 ml glass bottles or plastic bottles composed of, for example, polyether nitrile (PEN)] can be directly used as the anesthetic bottle 12.

The relief valve 38 suppresses the internal pressure of the mixed gas introduction passage to a level less than or equal to a predetermined pressure (first predetermined pressure) P being the upper limit of pressure level which does not impose a strain on the respiratory organs of the patient 14. With reference to FIG. 4(A) in detail, the relief valve 38 includes a valve casing 38a, a valve seat 38b, a valve body 38c, a handle 38d, an elastic member 38e, and a first exhaust port 38f.

The valve casing 38a is formed in a cylindrical shape and integrated with the outer surface of the hollow structure 34 so as to have an opening which enables its internal structure to be in communication with the hollow structure 34 through the first opening 34a smaller than this opening. The valve casing 38a has a female screw 38g partially formed on the inner surface of the valve casing 38a, and the female screw 38g mating with a male screw inserted from the tip of the valve casing 38 to the base end. The tip of the valve casing 38a protrudes to the outside and is formed into a flange 38h. The valve seat 38b is formed by narrowing the interior of the valve casing 38a on the base end side relative to the thread groove 38g toward the first opening 34a in the substantially hemispherical shape. The valve body 38c has a shape corresponding to the shape of the valve seat 38d; in a closed state in which the valve body 38c is seated on the valve seat 38b to close the first opening 34a, the valve body 38c eliminates the flow of a fluid from the first opening 34a to the gap between the valve body 38c and the valve seat 38b. The handle 38d is formed such that at least part of its outer surface threadably mates with the female screw 38g. The handle 38d is inserted while threadably mating with the female screw 38g and then moves toward the valve seat 38b. The elastic member 38e is, for instance, a spring and provided between the valve body 38c and the handle 38d to elastically urge the valve body 38c toward the valve seat 38b. In a valve-opened state in which the valve body 38c is separated from the valve seat 38b, gas flowing from the mixed gas introduction passage through the first opening 34a and the gap between the valve body 38c and the valve seat 38b is discharged from the first exhaust ports 38f to the exterior of the valve casing 38a. At least one first exhaust port 38f is formed in the inner surface of the valve casing 38a near the valve seat 38b so as to penetrate the valve casing 38a. For example, six first exhaust ports 38f are radially formed in the circumferential direction at even intervals as illustrated in FIG. 4(B). A predetermined pressure P can be adjusted by screwing the handle 38d into the valve casing 38a toward the base end the valve casing 38a to increase the elastic force against the valve body 38c or unscrewing the handle 38d toward the tip of the valve casing 38a to decrease the elastic force against the valve body 38c.

The relief valve 38 may have any other structure, such as structures having various mechanisms which can suppress the internal pressure of the mixed gas introduction passage to a level less than or equal to a predetermined pressure P [e.g., an adjustable pressure limiting valve (APL) valve used in typical artificial respirators]. Each of the valve seat 38b and valve body 38c may have any other shape which enables the entire valve body 38c to receive pressure in a valve-opened state in which the valve body 38c is separating from the valve seat 38b and enables the valve-opened state to be maintained until the internal pressure of the mixed gas introduction passage is reduced to PEEP being a second predetermined pressure relative to a first predetermined pressure (e.g., pressure being a fraction of a predetermine pressure P). The relief valve 38 may be provided to other components than the anesthesia attachment 24, such as the inhalation mask 18 and the artificial nose unit 20.

The sleeve 40 is formed in a cylindrical shape substantially coaxial with the valve casing 38a as illustrated in FIG. 4(A) such that the sleeve 40 can rotate around the valve casing 38a while the inner surface of the cylindrical structure abuts on the outer surface of the valve casing 38a. The sleeve 40 is provided between the hollow structure 34 and the flange 38h so as not to move in the axial direction.

The sleeve 40 has second exhaust ports 40a through which gas exhausted from the first exhaust ports 38f can flow out to the exterior of the sleeve 40. The second exhaust ports 40a may have a structure which enables the hollow structure 34 to be in communication with the exterior of the sleeve 40 through the first exhaust ports 38f and the second exhaust ports 40a in an opened state in which the second exhaust ports 40a are aligned with the first exhaust ports 38f by the rotation of the sleeve 40 around the valve casing 38a. A change in the rotational angle of the sleeve 40 with respect to the valve casing 38a can change the degree of the alignment of the first exhaust ports 38f with the second exhaust ports 40a, which can change the amount of the gas passing through the first exhaust ports 38f and the second exhaust ports 40a to increase or decrease the respiration rate of the patient 14. For example, in the case where the six first exhaust ports 38f are radially formed in the circumferential direction at even intervals as illustrated in FIG. 4(B), the second exhaust portions 40a may be formed so as to have the same structure. The left side of FIG. 4(B) illustrates the case in which the first exhaust ports 38f are fully aligned with the second exhaust ports 40a. In this case, the flow rate of the gas is the maximum as indicated by the width of white arrows. On the other hand, the right side of FIG. 4(B) illustrates the case in which the sleeve 40 is rotated around the valve casing 38a at 15°, and the degree of the alignment is reduced with the result that the flow rate of the gas is decreased. In other words, the sleeve 40 can function as a mechanism of adjusting the amount of discharged gas, in which the degree of closing of the first exhaust ports 38f of the relief valve 38 is sequentially changed to adjust the amount of the discharged gas.

The sleeve 40 has a bolt 40b which serves as a handle used to rotate the sleeve 40 or a stopper used to fix the rotational angle of the sleeve 40. The bolt 40b is externally screwed into the sleeve 40, and then its tip abuts on the outer surface of the valve casing 38a, so that the rotational movement of the sleeve 40 can be suppressed by frictional force.

The exhaust chamber 42 is formed, for example, in a wheel-like shape, and its inner circumference is attached to the outer surface of the sleeve 40 so as to enable relative rotation of the exhaust chamber 42. This configuration contributes to formation of hollow annular space 42a between the inner surface of the exhaust chamber 42 and the outer surface of the sleeve 40 including the second exhaust ports 40a, and gas exhausted from the second exhaust ports 40a is gathered in the space 42a without being directly released to the atmosphere. The exhaust chamber 42 has a third exhaust port 42b for discharging the gas gathered in the hollow annular space 42a to the anesthetic removal equipment 26. The exhaust chamber 42 may be provided to any other component than the sleeve 40 provided that space for gathering gas exhausted from the second exhaust ports 40a can be formed, for example, it may be rotatably attached to the valve casing 38a.

Figure 5:
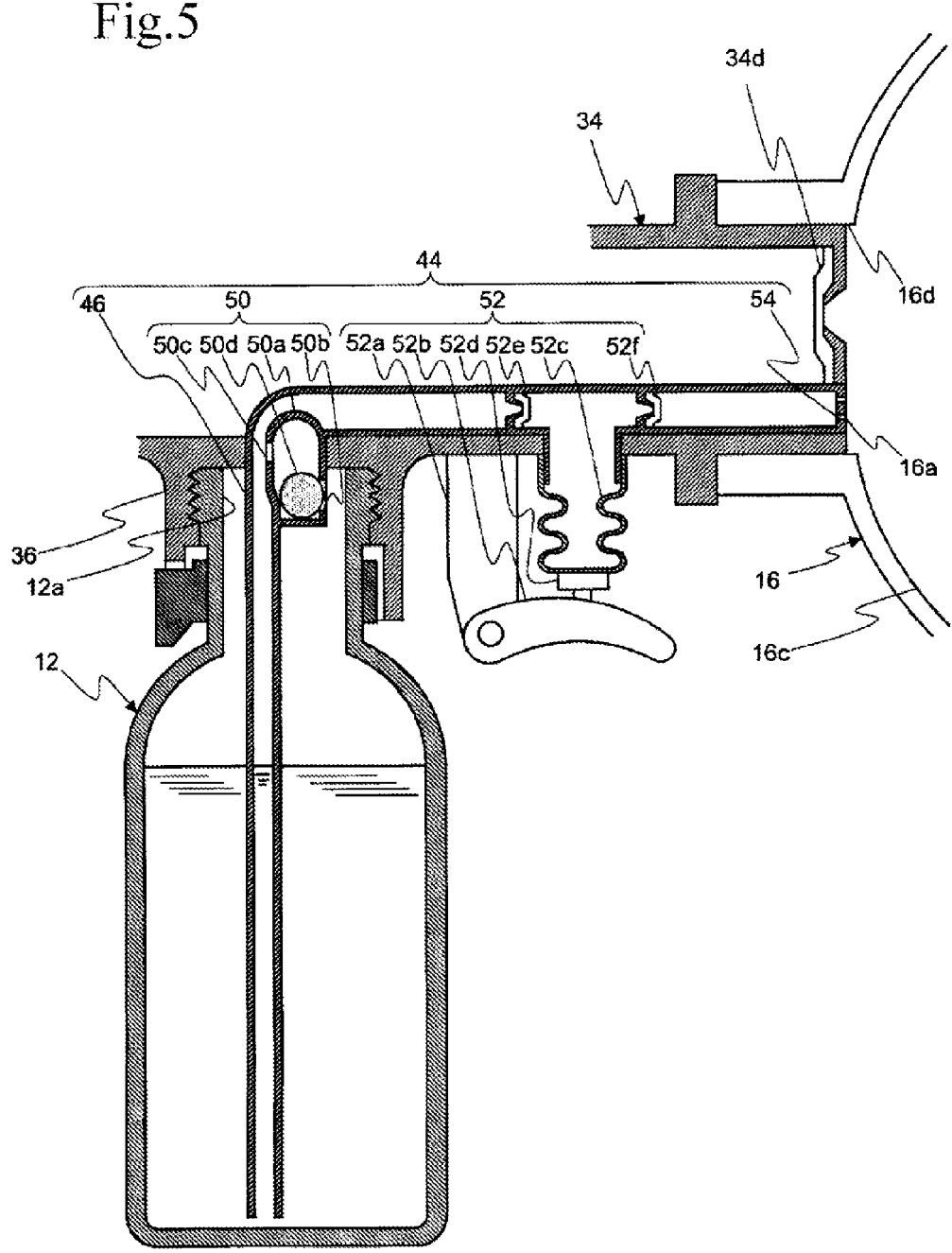
FIG. 5 is a partial cross-sectional view illustrating the detail of an anesthetic extraction unit.

The anesthetic extraction unit 44 serves to introduce an anesthetic held by the anesthetic bottle 12 into the anesthetic inlet 16a and includes an anesthetic extraction tube 46, an inverted supplying portion 50, a pump 52, and a nozzle 54 with reference to FIG. 5 in detail.

The anesthetic extraction tube 46 is connected to the connector 36 and is in communication with the interior of the anesthetic bottle 12 to function as an anesthetic extraction channel for unidirectionally introducing an anesthetic in the anesthetic bottle 12 into the anesthetic inlet 16a of the elastic bag 16. In the present embodiment, an end of the anesthetic extraction tube 46 extends to the bottom of the anesthetic bottle 12; on the other hand, the other end thereof extending from the interior of the anesthetic bottle 12 penetrates the bottom of the bottomed cylindrical structure of the connector 36 to intrude into the hollow structure 34 and extends from the intrusion point to the outlet port 16d of the elastic bag 16 through the interior of the hollow structure 34 to function as the anesthetic inlet 16a of the elastic bag 16. In particular, the anesthetic inlet 16a is formed so as to extend from the outlet port 16d to the mixing chamber 16c.

The pump 52 is used to pump out an anesthetic held by the anesthetic bottle 12 and then pump the anesthetic to the anesthetic inlet 16a of the elastic bag 16 through the anesthetic extraction tube 46. In the pump 52, a lever 52b rotatably attached to a supporting frame 52a vertically provided on the hollow structure 34 is rotated, which can contract a bellows cylinder 52c by application of pressure thereto via a connecting rod 52*d* connecting the lever 52*b* to the bellows cylinder 52*c*, the bellows cylinder 52*c* being in communicative connection with the anesthetic extraction tube 46 and being able to be elastically deformed to change its volume. In the anesthetic extraction tube 46, an inflow valve 52*e* is provided on the anesthetic bottle 12 side of the site with which the bellows cylinder 52*c* is in communicative connection, and an outflow valve 52*f* is provided on the anesthetic inlet 16*a* side of the same site. The inflow valve 52*e* allows an anesthetic in the anesthetic bottle 12 to unidirectionally flow into the bellows cylinder 52*c*, and the outflow valve 52*f* allows the anesthetic to unidirectionally flow out of the bellows cylinder 52*c* to the anesthetic inlet 16*a*. Each of the inflow valve 52*e* and the outflow valve 52*f* have a structure similar to that of the mixed gas inlet valve 34*d*, in which a rubber on-off valve is provided to the elastic bag 16 side of a through-hole narrowing the width of the anesthetic extraction channel 46. Each of the inflow valve 52*e* and the outflow valve 52*f* is the constituent of the pump 52. In order to prevent unintentional spraying of the anesthetic, the pump 52 may be provided with a safety mechanism which prevents the rotation of the lever 52*b*. For instance, a stopper pin (not illustrated) which can protrude from the supporting frame 52*a* to a plane of the rotation of the lever 52 may be provided to prevent the rotation of the lever 52*b* which compresses the bellows cylinder 52*c* being in an elongated state.

The nozzle 54 is provided in the anesthetic extraction tube 46 between the pump 52 and the anesthetic inlet 16*a*, in particular, between the outflow valve 52*f* and the anesthetic inlet 16*a*, and functions as an atomizing mechanism for atomizing the anesthetic pumped by the pump 52. The nozzle 54 has a barrier provided in the channel of the anesthetic extraction tube 46 to prevent the flow of the anesthetic and one or more pores formed in the barrier so as to form a communication between the outflow valve 52*f* in the channel of the anesthetic extraction tube 46 and the mixing chamber 16*c*. In the case where the anesthetic inlet 16*a* side of the anesthetic extraction tube 46 has a small diameter enough to atomize the anesthetic, the nozzle 54 may not be provided. In order to facilitate the atomization of the anesthetic, a heater (not illustrated) may be provided in the vicinity of the anesthetic extraction tube 46 to heat the anesthetic flowing in the tube. For example, an electric coil may be wound around the anesthetic extraction tube 46 in the vicinity of the nozzle 54 to apply electric current thereto, so that the anesthetic flowing in the anesthetic extraction tube 46 is heated by Joule heat to be generated.

The inverted supplying portion 50 enables an anesthetic in the anesthetic bottle 12 to be supplied to the pump 52 even in an inverted state in which the anesthetic outlet 12*a* of the anesthetic bottle 12 faces vertically downward. The inverted supplying portion 50 has an adjacent chamber 50*a* which adjoins the anesthetic extraction tube 46 at the bottom of the bottomed cylinder of the connector 36. The adjacent chamber 50*a* has a first continuous hole 50*b* which is in communication with the interior of the anesthetic bottle 12 and a second continuous hole 50*c* which is in communication with the anesthetic extraction tube 46 at a position away from the first continuous hole 50*b* in the direction of the opening of the anesthetic bottle 12. A ball 50*d* having a specific gravity larger than that of the anesthetic is movably accommodated in the adjacent chamber 50*a*, the ball 50*d* closing the first continuous hole 50*b* in an upright state in which the opening of the anesthetic bottle 12 faces vertically upward and not closing both first continuous hole 50*b* and the second continuous hole 50*c* in the inverted state.

The anesthetic gas concentration detector 28 is provided between the artificial nose unit 20 and the extension tube 22 as illustrated in FIG. 1 and directly detects the concentration of anesthetic gas content in gas in the mixed gas introduction passage; in other words, mainstream detection of the concentration of the anesthetic gas is carried out. The display 30 receives signals output from the anesthetic gas concentration detector 28 and related to the concentration of the anesthetic gas and shows the concentration of the anesthetic gas for users. The anesthetic gas concentration detector 28 is preferably provided to the mixed gas introduction passage at a position near the patient 14 to enhance accuracy in the detection of the concentration of anesthetic gas content in respiratory air of the patient 14; however, the anesthetic gas concentration detector 28 may not be provided between the artificial nose unit 20 and the extension tube 22 and can be provided to any other portion (e.g., between the anesthesia attachment 24 and the extension tube 22 or between the anesthesia attachment 24 and the elastic bag 16).

Examples of the anesthetic gas concentration detector 28 include a VEO multigas monitor (manufactured by PHASEIN AB) including a tube as a gas channel and an infrared concentration sensor provided to the exterior of the tube; in the case where the VEO multigas monitor is used, one end of the tube of the VEO multigas monitor is brought into communicative connection with the artificial nose unit 20 and the other end thereof is brought into communicative connection with the extension tube 22. The VEO multigas monitor is electrically connected to [e.g., universal serial bus (USB) connection] a computer (mobile personal computer such as CF-U1 manufactured by Panasonic Corporation) in which dedicated software for processing detection signals from the concentration sensor is installed, and the detection signals from the concentration sensor is transported to the computer. The computer functions as the display 30 which processes the received detection signals and shows the concentration of the anesthetic on its screen in real time. The computer connected to the VEO multigas monitor may be wired or wirelessly connected to an electrocardiograph, a sphygmomanometer, or a pulse oximeter and show various pieces of biological information, such as an electrocardiogram, blood pressure, or oxygen saturation, received from such medical equipment in real time, respectively. Users can also appropriately adjust anesthetic spraying frequency depending on information shown by the computer. It is desirable that the computer have an alarm (e.g., an alarm display on a computer screen or generation of a warning tone) which notifies users of information transmitted from the medical equipment in the case where a specific condition is satisfied, such as the case in which the concentration of an anesthetic, a heart rate, or blood pressure exceeds a certain level.

Although the mainstream concentration detector is employed as the anesthetic gas concentration detector 28, a sidestream concentration detector may be employed in place of it, in which gas is extracted from the interior of the mixed gas introduction passage (e.g., the interior of the artificial nose unit 20 or the anesthesia attachment 24) to detect the concentration of an anesthetic content in the gas with a concentration sensor incorporated into the anesthetic gas concentration detector separately provided.

The operation of the anesthetic inhalation aid device 10 having such a configuration will now be described.

In the case where the lever 52*b* is moved up in the upright state of the anesthesia attachment 24, pressure is applied to the bellows cylinder 52*c* via the connecting rod 52*d* connected to the lever 52*b* to contract the bellows cylinder 52*c*.

Figure 6:
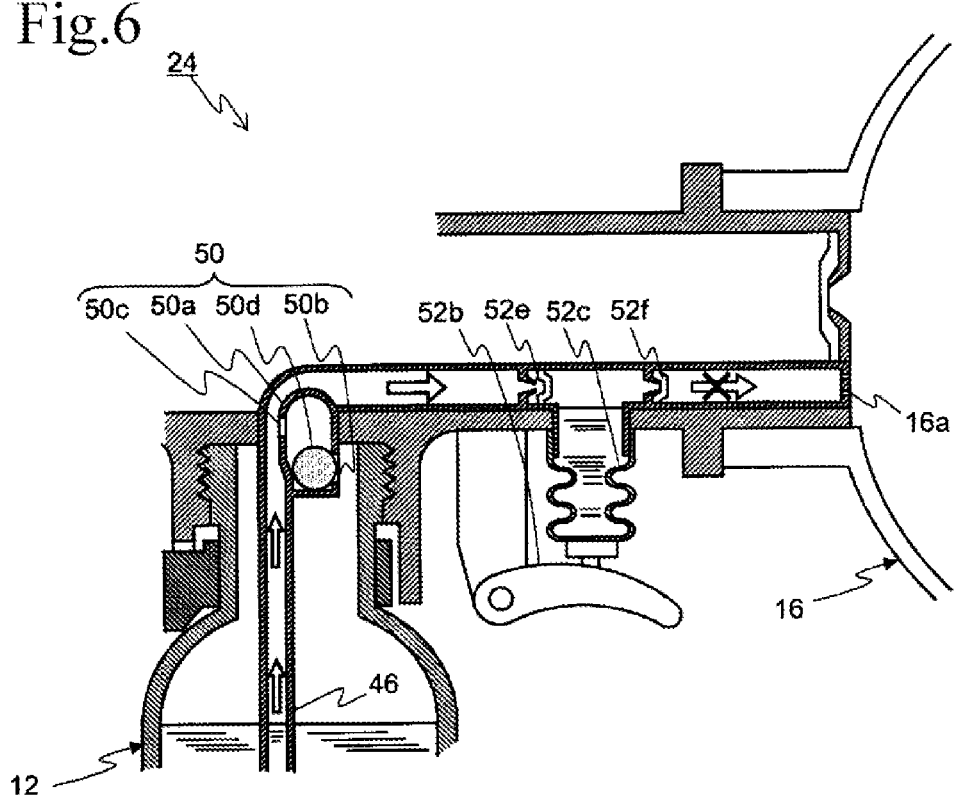
FIG. 6 is a first step in a process of administrating an anesthetic.

The bellows cylinder 52c expands while an elastic force of the bellows cylinder 52c returns the lever 52b to the original position as illustrated FIG. 6, which generates negative pressure inside the bellows cylinder 52c. Since the outflow valve 52f blocks a flow from the anesthetic inlet 16a to the anesthetic bottle 12, the negative pressure generated in the bellows cylinder 52c enables only the inflow valve 52e to be opened, and then an anesthetic held by the anesthetic bottle 12 is introduced into the interior of the bellows cylinder 52c through the anesthetic extraction tube 46. In this case, the first continuous hole 50b of the inverted supplying port 50 is closed by the ball 50d, so that the anesthetic which has entered the adjacent chamber 50a from the second continuous hole 50c during the introduction does not pass through the first continuous hole 50b to return to the interior of the anesthetic bottle 12.

Figure 7:
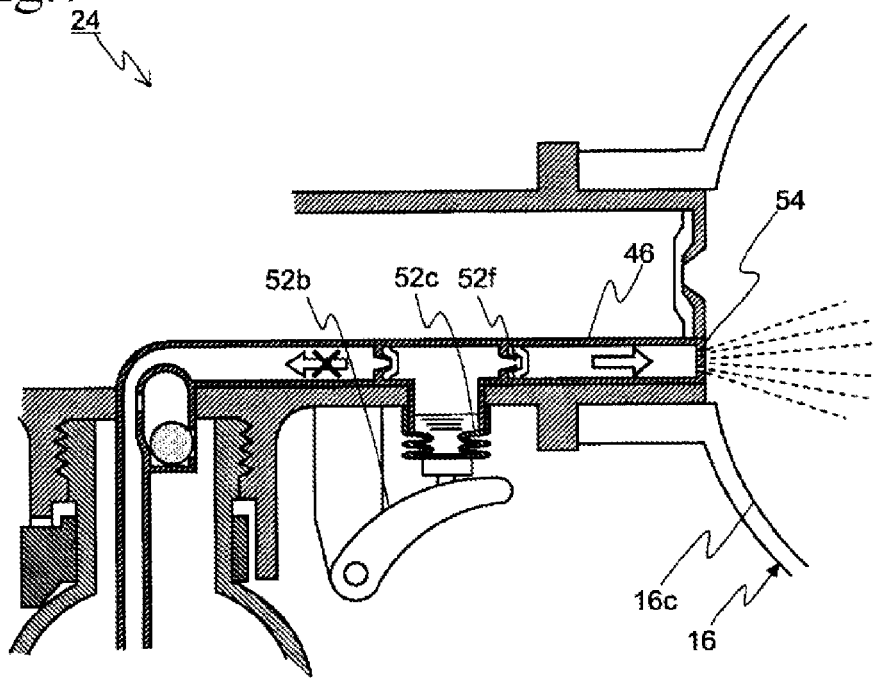
FIG. 7 is a second step in the process of administrating an anesthetic.

Moving up the lever 52b again contracts the bellows cylinder 52c to apply pressure to the anesthetic introduced into the interior of the bellows cylinder 52c as illustrated in FIG. 7. The application of pressure enables the anesthetic in the bellows cylinder 52c to compressively separate the on-off valve of the outflow valve 52f from the through-hole into a valve-opened state. The anesthetic flows in the anesthetic extraction tube 46 as indicated by a white arrow and is then sprayed into the mixing chamber 16c through the pores of the nozzle 54, resulting in being quickly atomized.

Figure 8:
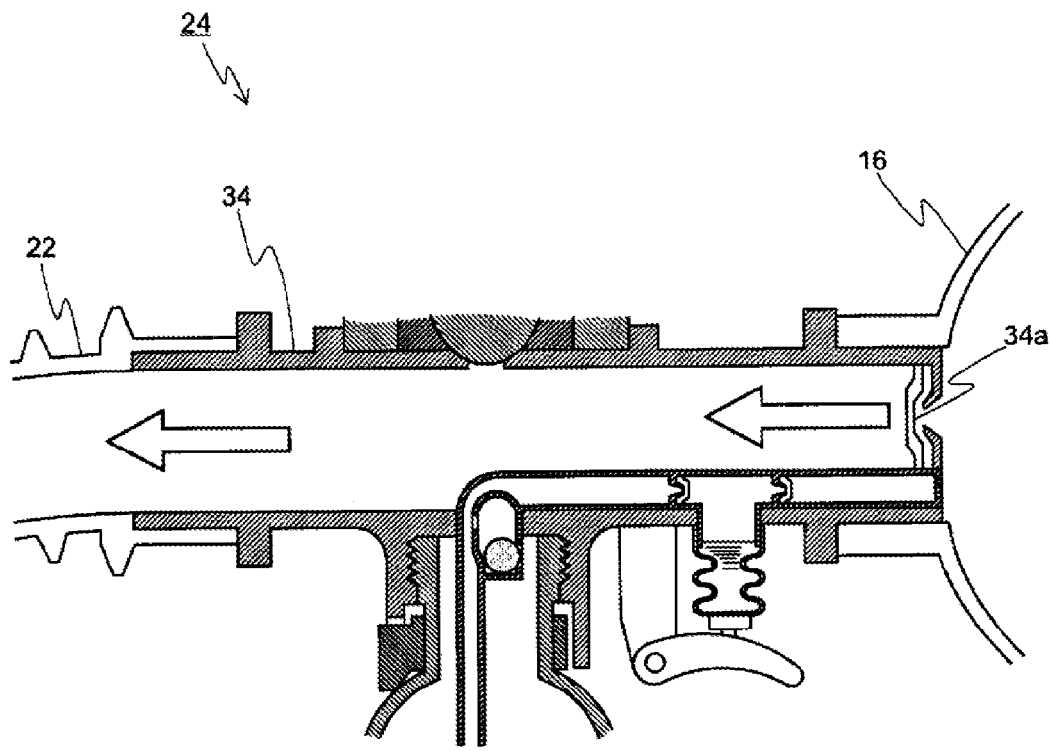
FIG. 8 is a third step in the process of administrating an anesthetic.

The atomized anesthetic is mixed with oxygen gas introduced from the air inlet 16b or the like in the mixing chamber 16c into mixed gas. The mixed gas flows into the hollow structure 34 of the anesthesia attachment 24 through the mixed gas inlet valve 34d as indicated by white arrows in FIG. 8 and then is introduced into the extension tube 22 and the inhalation mask 18, the mixed gas inlet valve 34d being opened by manual compression of the elastic gag 16, inspiratory pressure generated by the spontaneous respiration of the patient 14, or transportation of compressed oxygen or compressed air from a pressure container (if needed) to the mixing chamber 16c at a certain flow rate (e.g., 10 liters per minute), the pressure container being connected to the spare inlet 16e and holding oxygen or air.

In the case where the gas pressure in the mixed gas introduction passage reaches a predetermined pressure P, biasing force applied to the valve body 38c of the relief valve 38 by the elastic body 38e cannot resist the gas pressure, and the valve body 38c is therefore separated from the valve seat 38b. Thus, part of the gas in the mixed gas introduction passage flows from the first exhaust ports 38f to the interior of the space 42a of the exhaust chamber 42 through the second exhaust ports 40a of the sleeve 40. The gas flows from the third exhaust port 42b to the interior of the anesthetic removal equipment 26 through the exhaust tube 32 and then is released to the atmosphere after the anesthetic content is removed. The mixed gas inlet valve 34d prevents the flow of the expired air of the patient 14 into the mixing chamber 16c of the elastic bag 16. Through these processes, the internal pressure of the mixed gas introduction passage is suppressed to a certain level or lower, which reduces the strain on the respiratory organs of the patient 14 and facilitates removal of carbon dioxide contained in the expired air of the patient 14. The inspiratory flow rate of the patient 14 can be adjusted by rotating the sleeve 40 around the valve casing 38a to change the degree of alignment of the first exhaust ports 38f with the second exhaust ports 40a as described above. In the case where a pressure container holding oxygen or air is connected to the spare inlet 16e to transport compressed oxygen or compressed air from the pressure container to the mixing chamber 16c at a certain flow rate (e.g., 10 liters per minute), artificial respiration can be automatically carried out, and, in addition to the rotation of the sleeve 40, an increase or decrease in a rate of air supply can adjust the frequency of ventilation (the same holds for the below description).

Figure 9:
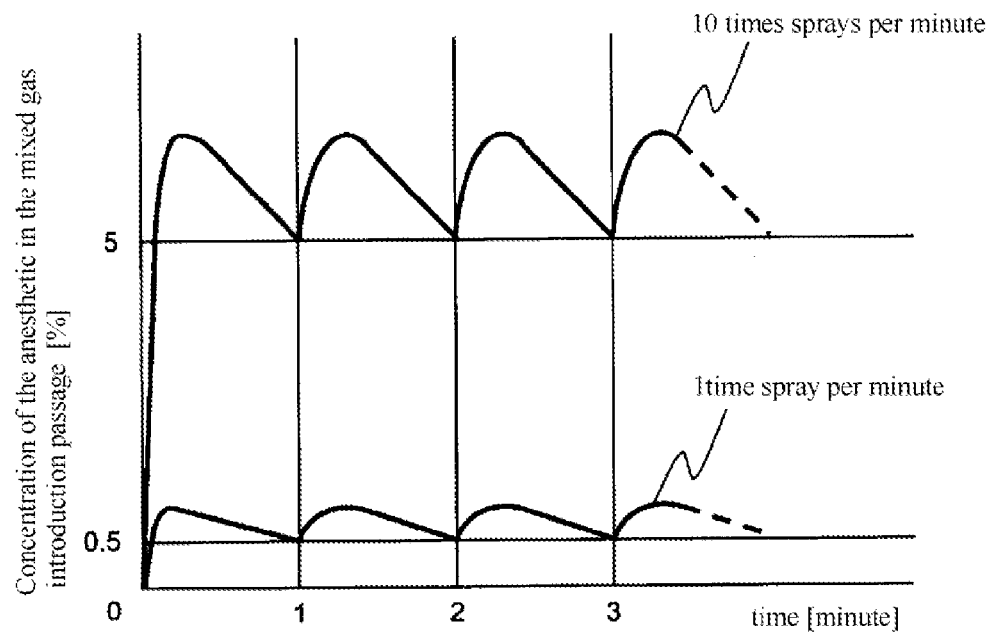
FIG. 9 illustrates the frequencies of spray of an anesthetic.

The frequency at which an anesthetic is sprayed with the pump 52 can be varied depending on an intended depth of anesthesia as illustrated in FIG. 9. Depending on the amount of an anesthetic sprayed by a single operation of the pump 52, for instance, in the case where the concentration of the anesthetic in the mixed gas introduction passage is determined as approximately 0.5% to administer the anesthetic in a minimum amount enough to make the patient 14 unconscious, the anesthetic is sprayed once a minute. In contrast, for example, in the case where the concentration of the anesthetic is determined as approximately 5% to increase the depth of anesthesia when the patient 14 has developed a serious symptom, the anesthetic is sprayed approximately 10 times a minute.

Even though an anesthetic is sprayed at a predetermined frequency, the concentration of the anesthetic in the mixed gas introduction passage varies depending on the vital capacity and respiratory frequency of the patient 14, which may cause a variation in the depth of anesthesia between individual patients. Hence, anesthetic spray frequency is appropriately determined through observation of the concentration of anesthetic gas shown by the display 30 which receives signals related to the concentration of the anesthetic gas from the anesthetic gas concentration detector 28. The anesthetic gas concentration detector 28 is a mainstream concentration detector as described above and can control the anesthetic spray frequency by highly responsive and accurate detection of the concentration of anesthetic gas.

The operation of the anesthetic inhalation aid device 10 in the inverted state will now be described. Description of the same operation as in the upright state will be omitted.

Figure 10:
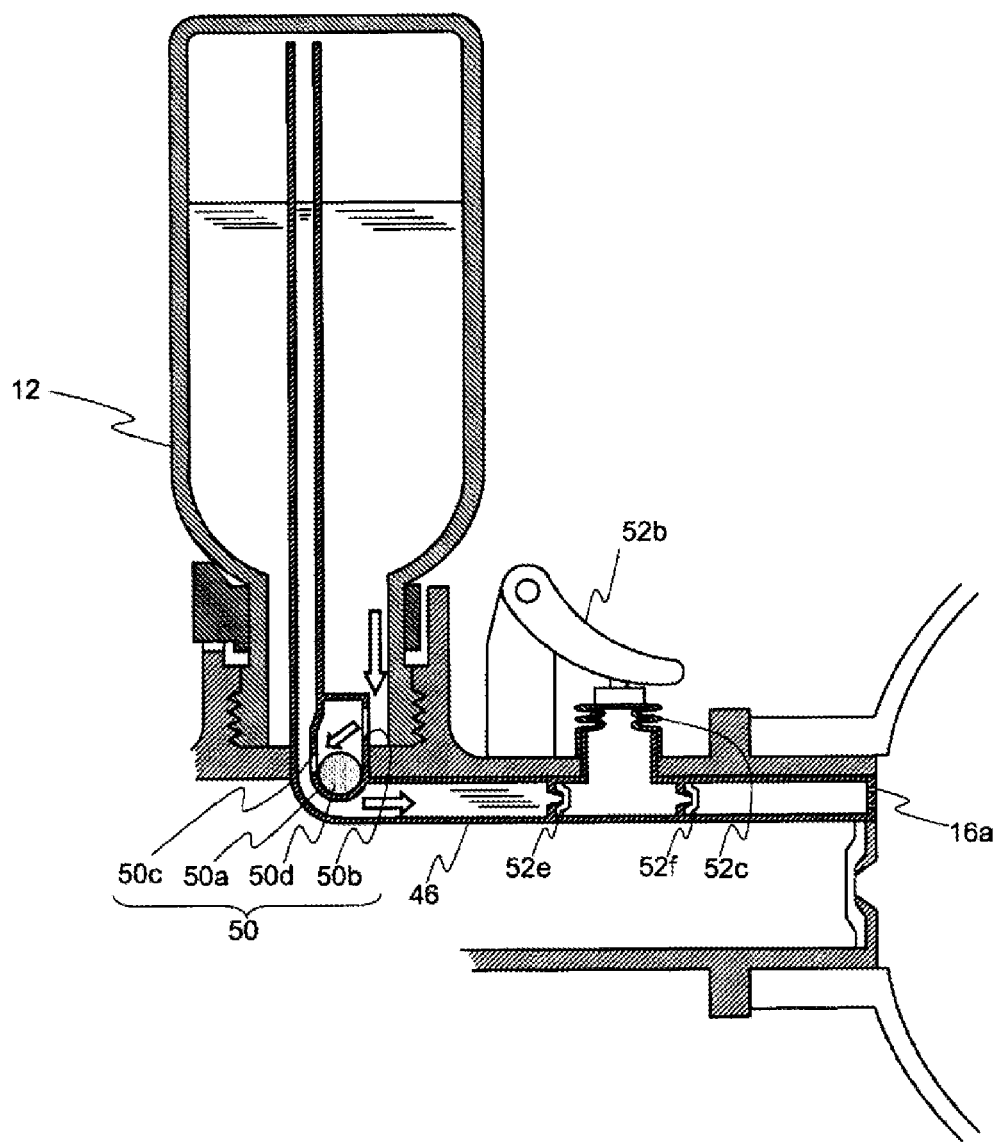
FIG. 10 illustrates a procedure of administrating an anesthetic in an inverted state.

As illustrated in FIG. 10, the lever 52b is moved down to contract the bellows cylinder 52c, and pressure is applied to the interior thereof. In this state, the ball 50d in the inverted supplying portion 50, which has a specific gravity larger than that of anesthetic, separates from the first continuous hole 50b and has fallen to the bottom of the adjacent chamber 50a without closing the second continuous hole 50c. Thus, the anesthetic held by the anesthetic bottle 12 enters the adjacent chamber 50a from the first continuous hole 50b and then is introduced into the anesthetic extraction tube 46 through the second continuous hole 50c as indicated by white arrows. Since pressure has been applied to the interior of the bellows cylinder 52c, the introduced anesthetic cannot pass through the outflow valve 52e.

Then, the bellows cylinder 52c expands while an elastic force of the bellows cylinder 52c returns to the lever 52b to the original position, which generates negative pressure inside the bellows cylinder 52c. Since the outflow valve 52f blocks a flow from the anesthetic inlet 16a to the anesthetic bottle 12, the negative pressure generated in the bellows cylinder 52c enables only the inflow valve 52e to be opened, and the anesthetic which has flown right before the inflow valve 52e is introduced into the bellows cylinder 52c.

The anesthesia attachment 24 connected to the anesthetic bottle 12 is incorporated into a typical manual artificial respirator generally used in almost all medical institutions, and an anesthetic is manually sprayed in synchronism with artificial respiration, so that the anesthetic inhalation aid device 10 enables inhalation administration of the anesthetic. Hence, the anesthetic inhalation aid device 10 having a compact size has excellent portability and storability, is easy to handle, and contributes to a significant reduction in introduction cost, as compared with traditional large-scale inhalational anesthesia systems. Moreover, unlike typical inhalational anesthesia systems used only in a medical environment fully equipped with, for example, stable power sources and gas pipes, the aesthetic inhalation aid device 10 does not require power sources or supply of carrier gas as in traditional manual artificial respirators. Accordingly, the anesthetic inhalation aid device 10 can not only be widely introduced into, for example, small medical institutions such as medical or dental clinics, public institutions, business establishments, schools, and ordinary households, but may also be installed in transporters such as railroad vehicles, automobiles, airplanes, and ships. The introduced/installed anesthetic inhalation aid device 10 can be used for prompt and easy inhalation administration of anesthetics not only by a doctor but also by a nurse, an emergency medical technician, or any other person than a doctor under the supervision and instruction by a doctor. Even if the anesthetic inhalation aid device 10 is not provided in the vicinity of the patient 14 being in a convulsive state, the anesthetic inhalation aid device 10 can be brought to the patient 14 to administer inhalational anesthetics, which can protect the brain at an early stage and minimize damage to the brain brought by delayed treatment. Furthermore, even in the event of a power failure, a disaster, or the like when it is difficult to secure power sources or supply carrier gas, the anesthetic inhalation aid device 10 securely enables inhalation administration of anesthetics.

In particular, as compared with typical inhalational anesthesia systems, the anesthetic inhalation aid device 10 enhances capability of terminating convulsions at an earlier stage in addition to its inherent advantage of capability of safe treatment during airway management. The anesthetic inhalation aid device 10 therefore contributes to an enhancement in a survival rate of the patient 14 and prevention of aftereffects caused by brain disorders due to status epilepticus. In addition, the anesthetic inhalation aid device 10 enables prompt and easy inhalation administration of anesthetics to the patient 14 being in status epilepticus as well as every patient 14 for whom sedation or analgesic treatment by inhalational anesthesia is considered to be effective.

In a weightless environment as in the International Space Station or a manned spacecraft in space, administration of anesthetics has an extremely high risk of causing unstable cardiorespiratory functions. It is therefore ideal to use medications which enable adjustment of the depth of anesthesia, such as inhalational anesthetics. In addition, inhalational anesthetics are nonflammable, and use of the anesthetic inhalation aid device 10 enables administration of anesthetics without pollution of ambient air; hence, the anesthetic inhalation aid device 10 can be safely used even in a narrow closed space. Furthermore, the anesthetic inhalation aid device 10 has a weight smaller than that of electric syringe pumps necessary for intravenous anesthesia, which contributes a reduction in cost required for transportation to outer space.

The anesthetic inhalation aid device 10 can also be readily introduced into veterinary hospitals and provides the same advantages to inhalational anesthesia for animals other than humans as in inhalational anesthesia for humans.

Figure 11:
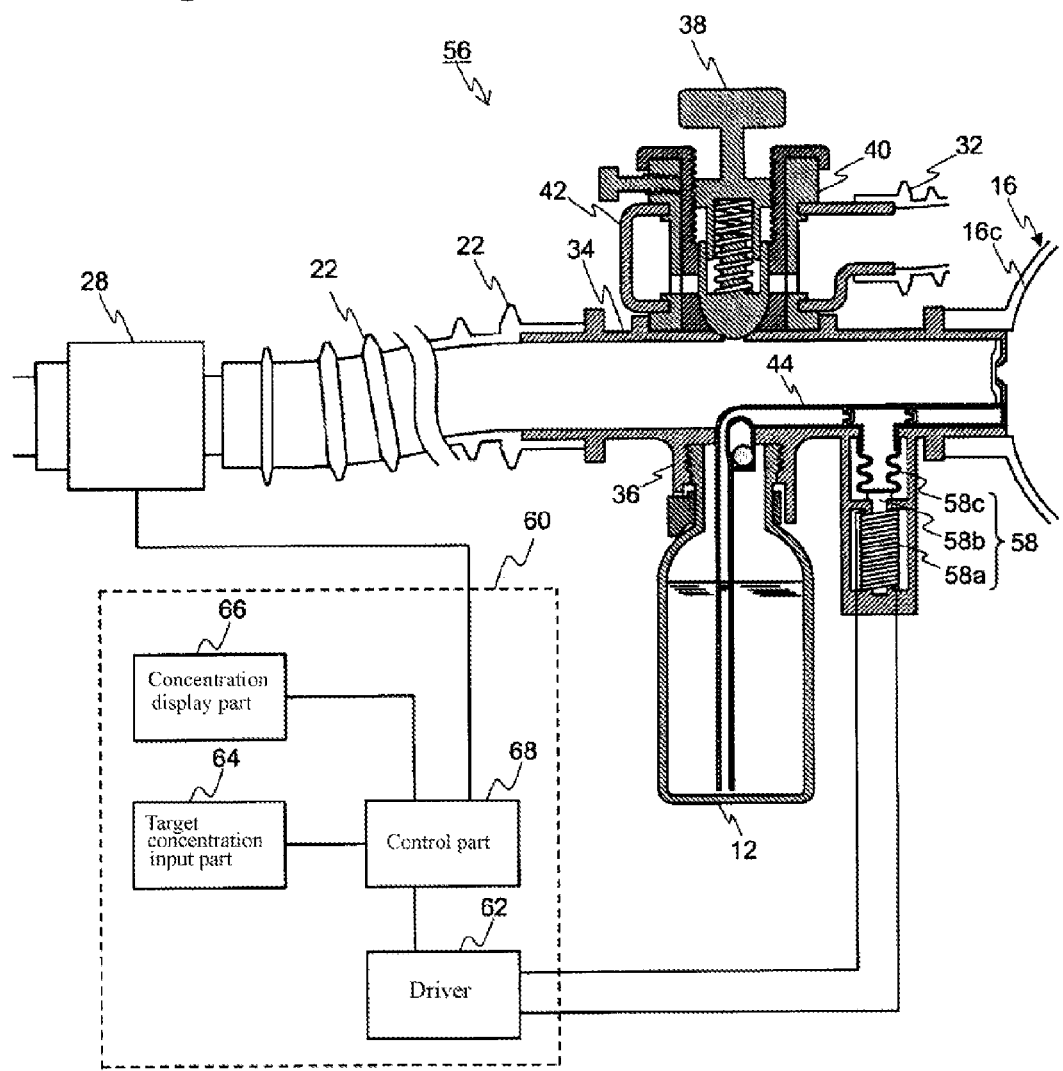
FIG. 11 illustrates an example of an anesthetic inhalation aid device according to a second embodiment of the present invention.

An example of an anesthetic inhalation aid device according to a second embodiment will now be described with reference to FIG. 11. The same configurations as used in the first embodiment are denoted by the same symbols, and description thereof will be omitted or abbreviated.

The anesthetic inhalation aid device 10 includes an anesthesia attachment 56 having a pump 58 in place of the anesthesia attachment 24 having the pump 52. Instead of the manual lever 52b of the pump 52, the pump 58 has an actuator fixed under a bellows cylinder 58c and having a solenoid 58a and a movable iron core 58b inserted thereinto. The bellows cylinder 58c of the pump 58 is connected to an end of the movable iron core 58b. The actuator functions as an actuation unit in which the solenoid 58a repeatedly enters an electrified state and a non-electrified state with the result that the movable iron core 58b expands and contracts the bellows cylinder 58c to activate the pump 58. The actuator may have a structure in which the bellows cylinder 58c is expanded and contracted with a motor being a power source.

The anesthesia attachment 56 is integrated with an anesthetic gas concentration control unit 60 to automatically control the concentration of an anesthetic. The anesthetic gas concentration control unit 60 includes a driver 62, a target concentration input part 64, a concentration display part 66, and a control part 68.

The driver 62 functions as a driving circuit which receives electric power from a power source provided to the anesthetic inhalation aid device 10, such as a battery, or from a commercially available power source to electrify the solenoid 58a and then drives the actuator. For instance, the driver 62 has a switching device such as a transistor, and the switching device is turned on and off to shift the state of the solenoid 58 between an electrified state and a non-electrified state.

The target concentration input part 64 is an input unit used for inputting a target concentration Cs of an anesthetic to be administered to the patient 14 in the depth of anesthesia suitable for a symptom of the patient 14 and also is a start/stop unit to start/stop the operation of the anesthetic gas concentration control unit 60. For example, a touch-screen liquid crystal panel is used in the target concentration input part 64. In such a liquid crystal panel, users can touch predetermined images (icons) to input a target concentration. It is preferred that the target concentration input part 64 have a function to cancel the input only with a specific operation in order to prevent the unintended operation of the anesthetic gas concentration control unit 60 or a wrong change in the input of a target concentration Cs during the operation of the anesthetic gas concentration control unit 60.

The concentration display part 66 shows a target concentration Cs input from the target concentration input part 64 and a detection concentration Ct of an anesthetic detected by the anesthetic gas concentration detector 28. A liquid crystal panel is, for instance, used in the concentration display part 66; in this case, the same liquid crystal panel may be used for both the concentration display part 66 and the target concentration input part 64, and a display mode is changed between a target concentration input mode and anesthetic concentration display mode or the like.

The control part 68 having a built-in computer receives signals of a detection concentration Ct from the anesthetic gas concentration detector 28 and signals of a target concentration Cs from the target concentration input part 64. The control part 68 outputs signals for showing the anesthetic concentration to the concentration display part 66 in response to the signals of a detection concentration Ct from the anesthetic gas concentration detector 28. The control part 68 runs a control program stored in a read only memory (ROM) to function as a control circuit which controls the driver 62 on the basis of the detection concentration Ct detected by the anesthetic gas concentration detector 28 and a predetermined target concentration Cs input from the target concentration input part 64.

Figure 12:
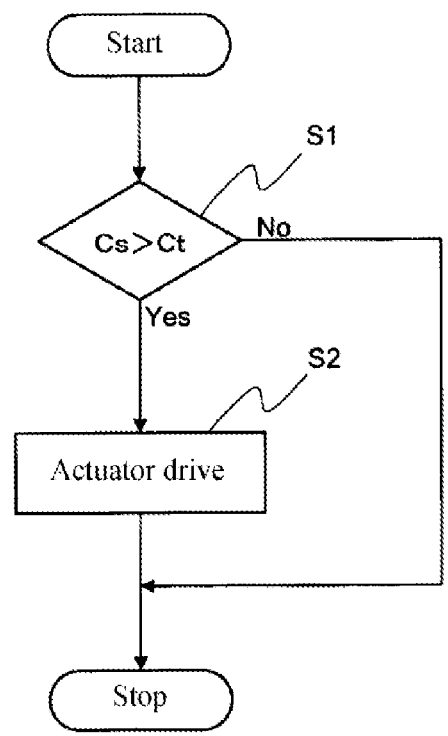
FIG. 12 is a flow diagram illustrating a control process in the second embodiment.

FIG. 12 illustrates a control process of the control program in the control part 68, the control program being repeatedly run from the start of the operation of the anesthetic gas concentration control unit 60 to the stop thereof for every time $\Delta t$. Time $\Delta t$ is determined to maintain an average anesthetic concentration necessary for the patient 14 on the basis of the volume of the mixing chamber 16c of the elastic bag 16, an amount of air inspired by the patient 14 at single inspiration, and a single spraying amount of the pump 58.

In Step 1 (abbreviated as "S1" in the drawing, the same holds for the following description), the magnitude of a detection concentration Ct detected by the anesthetic gas concentration detector 28 is compared with the magnitude of a target concentration Cs input from the target concentration input part 64. In the case where the detection concentration Ct is smaller than the target concentration Cs, the procedure enters Step 2 (Yes) to spray an anesthetic; in contrast, in the case where the detection concentration Ct is greater than or equal to the target concentration Cs, the control process terminates (No) without carrying out the spraying of an anesthetic.

In Step 2, driving signals are output from the control part 68 to the driver 62 to drive the actuator with the solenoid 58a.

The anesthetic inhalation aid device 10 of the second embodiment can contribute to anesthetic management without complicated handling as compared with the configuration of the first embodiment in which the pump 52 is manually operated with the lever 52b to spray an anesthetic. In particular, in the anesthetic inhalation aid device 10 of the second embodiment, since the anesthetic gas concentration control unit 60 observes the concentration of an anesthetic content in inspired and expired air every predetermined time and automatically controls the operation of the actuator to maintain a predetermined concentration, which eliminates the operation of the lever 52b and makes entire operation less complicated. Particularly in the case where the operation of the elastic bag 16 must be also carried out in parallel when the spontaneous respiration of the patient 14 is weak, the complexity of the operation can be remarkably reduced.

In the second embodiment, the target concentration input part 64, the concentration display part 66, and the control part 68 may be incorporated into a mobile personal computer, such as CF-U1 manufactured by Panasonic Corporation, as an example of the display 30 of the first embodiment. The computer may be connected to medical equipment for analyzing biological information so as to have communication with each other and may receive various pieces of biological information, such as an electrocardiogram, blood pressure, or oxygen saturation, from the medical equipment as described in the first embodiment, in addition to information on concentration output from the anesthetic gas concentration detector 28. The various pieces of received biological information are shown by the concentration display part 66 in real time via the control part 68. The control part 68 forces the active control program to terminate to stop the spraying of an anesthetic in the case where a specific condition is satisfied, such as the case in which a heart rate or blood pressure obtained from the medical equipment exceeds a certain level. The control part 68 may be configured such that the spraying of an anesthetic can be restarted only with a predetermined procedure after the forced termination. The control part 68 instructs the concentration display part 66 to exhibit a notification to give notice of the predetermined condition being satisfied. The predetermined condition may be input with the target input portion 60. Such a configuration enables the anesthetic inhalation aid device 10 not only to observe the concentration of an anesthetic but to carry out anesthetic management in a comprehensive consideration of the biological information of the patient 14.

Although the pump 58 is operated with the actuator in the second embodiment, the pump 58 may be configured so as to be operated with the lever 52b as in the first embodiment. Such a configuration, for example, enables an anesthetic to be manually sprayed in the case where electric power is less likely to be supplied to the anesthetic gas concentration control unit 60.

Figure 13:
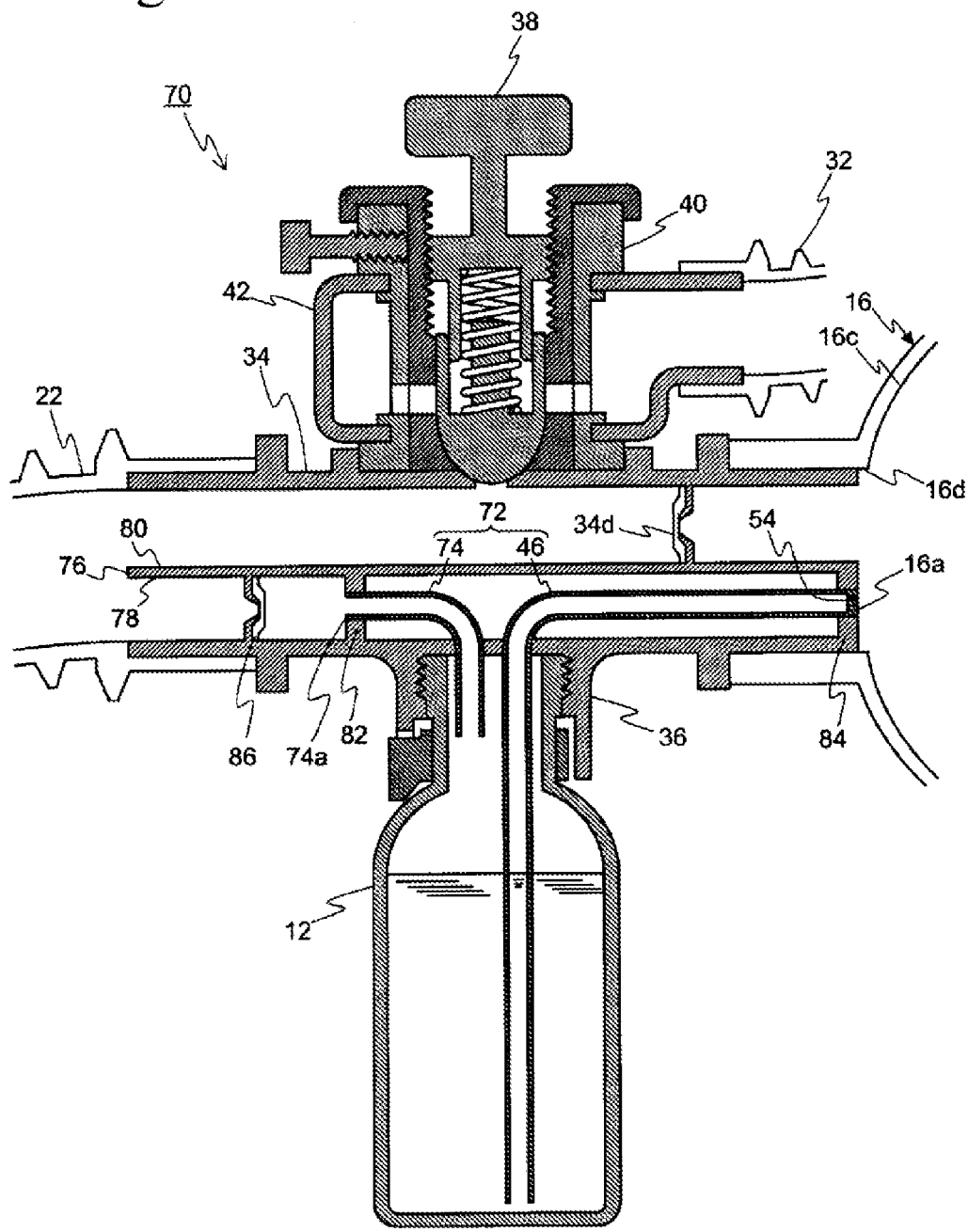
FIG. 13 is a partial cross-sectional view illustrating an example of an anesthetic inhalation aid device according to a third embodiment of the present invention.

An example of an anesthetic inhalation aid device according to a third embodiment will now be described with reference to FIG. 13. The same configurations as used in the first embodiment are denoted by the same symbols, and description thereof will be omitted or abbreviated.

The anesthetic inhalation aid device 10 includes an anesthesia attachment 70 in place of the anesthesia attachment 24. The anesthesia attachment 70 includes an anesthetic extraction unit 72 having an expired air introduction tube 74 to introduce the expired air of the patient 14 into the inner space of the anesthetic bottle 12. The expired air introduction tube 74 extends from the interior of the anesthetic bottle 12, penetrates the bottom of the bottomed cylinder of the connector 36, and then enters the hollow structure 34 of the anesthesia attachment 70. The expired air introduction tube 74 extends in the hollow structure 34 from the entrance position toward the extension tube 22, and its extended side opening functions as an expired air inlet 74a formed so as to face the expired air of the patient 14. The anesthetic extraction unit 72 does not include the pump 52 of the first embodiment.

The inner space of the hollow structure 34 of the anesthesia attachment 70 can be divide into a first tube 78 and a second tube 80 by a partition 76 extending from the outlet port 16d of the elastic bag 16 toward the extension tube 22.

In the first tube 78, a first internal flange 82 is formed in the vicinity of the expired air inlet 74a so as to extend from the inner surface of the tube 78 to the outer surface of the expired air introduction tube 74, and a second internal flange 84 is formed in the vicinity of the anesthetic inlet 16a of the elastic bag 16 so as to extend from the inner surface of the tube 78 to the outer surface of the anesthetic introduction tube 46. The first internal flange 82 and the second internal flange 84 prevent a gas flow in the first tube 78 between the elastic bag 16 and the extension tube 22. An anesthetic check valve 86 is provided in the channel of the first tube 78 to prevent the backflow of an anesthetic held by the anesthetic bottle 12 to the extension tube 22 through the expired air introduction tube 74.

The mixed gas inlet valve 34d is provided in the channel of the second tube 80 on the side of the outlet port 16d relative to the relief valve 38. The anesthetic check valve 86 has a structure similar to that of the mixed gas inlet valve 34d. The expired air introduction tube 74 and the anesthetic check valve 86 constitute an expired air-introducing channel for unidirectionally introducing the expired air of the patient 14 into the inner space of the anesthetic bottle 12.

The operation of the anesthetic inhalation aid device 10 of the third embodiment will now be described.

The expired air of the patient 14 is introduced from the extension tube 22 into the first tube 78 and second tube 80 of the anesthesia attachment 70.

The expired air introduced into the first tube 78 applies pressure to the anesthetic check valve 86 to open the same and then is introduced from the expired air inlet 74a into the anesthetic bottle 12 with the guidance of the expired air introduction tube 74. Secretions contained in the expired air of the patient 14 are collected by the artificial nose filter inserted into the artificial nose unit 20 and do not therefore substantially enter the anesthetic bottle 12.

The expired air introduced into the anesthetic bottle 12 applies pressure to an anesthetic held by the anesthetic bottle 12. The pressurized anesthetic is pumped out of the interior of the anesthetic bottle 12 to the nozzle 54 through an end of the anesthetic extraction tube 46, the nozzle 54 being provided at the other end thereof. The pressurized anesthetic is sprayed from the nozzle 54 into the mixing chamber 16c of the elastic bag 16 and then vaporized.

The vaporized anesthetic is mixed with oxygen gas introduced from the air inlet 16b or the like in the mixing chamber 16c to generate mixed gas. The mixed gas flows into the channel of the second tube 80 of the anesthesia attachment 70 through the mixed gas inlet valve 34d and then is introduced into the extension tube 22 and the inhalation mask 18, the mixed gas inlet valve 34d being opened by manual compression of the elastic gag 16, inspiratory pressure generated by the spontaneous respiration of the patient 14, or transportation of compressed oxygen or compressed air from a pressure container (if needed) to the mixing chamber 16c at a certain flow rate (e.g., 10 liters per minute), the pressure container being connected to the spare inlet 16e and holding oxygen or air. The anesthetic check valve 86 prevents the anesthetic gas vaporized in the anesthetic bottle 12 from flowing toward the extension tube 22 and therefore prevents a reduction in the internal pressure of the anesthetic bottle 12, which can prevent the mixed gas in the mixing chamber 16c from flowing into the anesthetic bottle 12 through the anesthetic extraction tube 46.

In the anesthetic inhalation aid device 10 of the third embodiment, utilization of the expired air of the patient 14 enables an anesthetic in the anesthetic bottle 12 to be sprayed and then vaporized. Hence, as compared with the anesthetic inhalation aid device 10 of the first embodiment, the anesthetic in the anesthetic bottle 12 can be sprayed without use of the pump 52, which can reduce the weight of the anesthetic inhalation aid device 10 and complexity of the operation with the lever 52b.

An example of an anesthetic inhalation aid device according to a fourth embodiment will now be described with reference to FIGS. 14 to 17. The same configurations as used in the first embodiment are denoted by the same symbols, and description thereof will be omitted or abbreviated.

Figure 14:
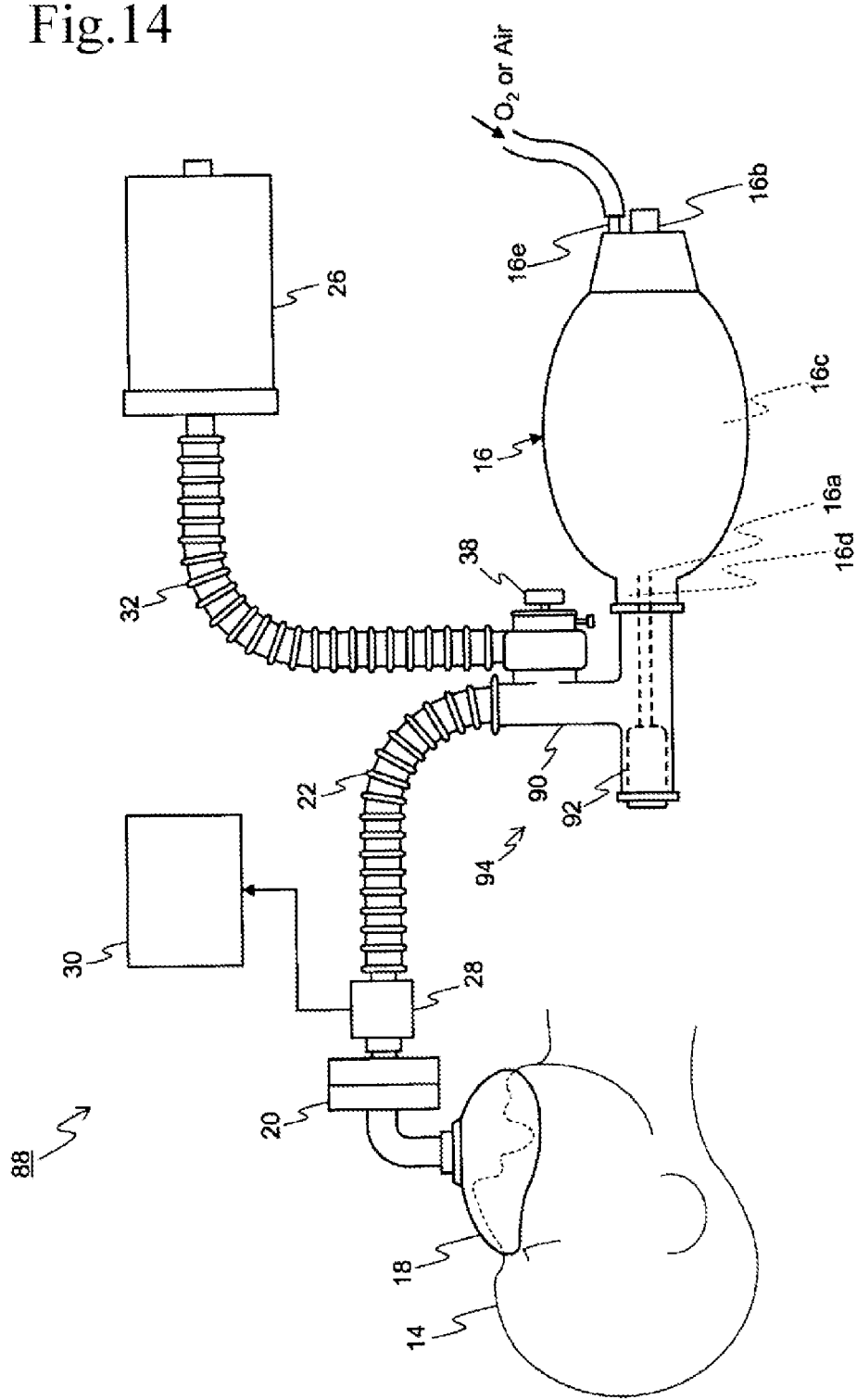
FIG. 14 is a general view illustrating an example of an anesthetic inhalation aid device according to a fourth embodiment of the present invention.

With reference to FIG. 14, an anesthetic inhalation aid device 88 of the present embodiment includes an anesthesia attachment 94 having the relief valve 38, a hollow structure 90, and a vaporization injector syringe (Vapo-Ject) 92, in addition to the elastic bag 16, the inhalation mask 18, the artificial nose unit 20, the extension tube 22, the anesthetic removal equipment 26, the anesthetic gas concentration detector 28, the display 30, and the exhaust tube 32. In the present embodiment, the above-mentioned pressure container holding the oxygen or air is connected to the spare inlet 16e of the elastic bag 16, and the oxygen gas or air is introduced from the pressure container into the mixing chamber 16c.

Figure 15:
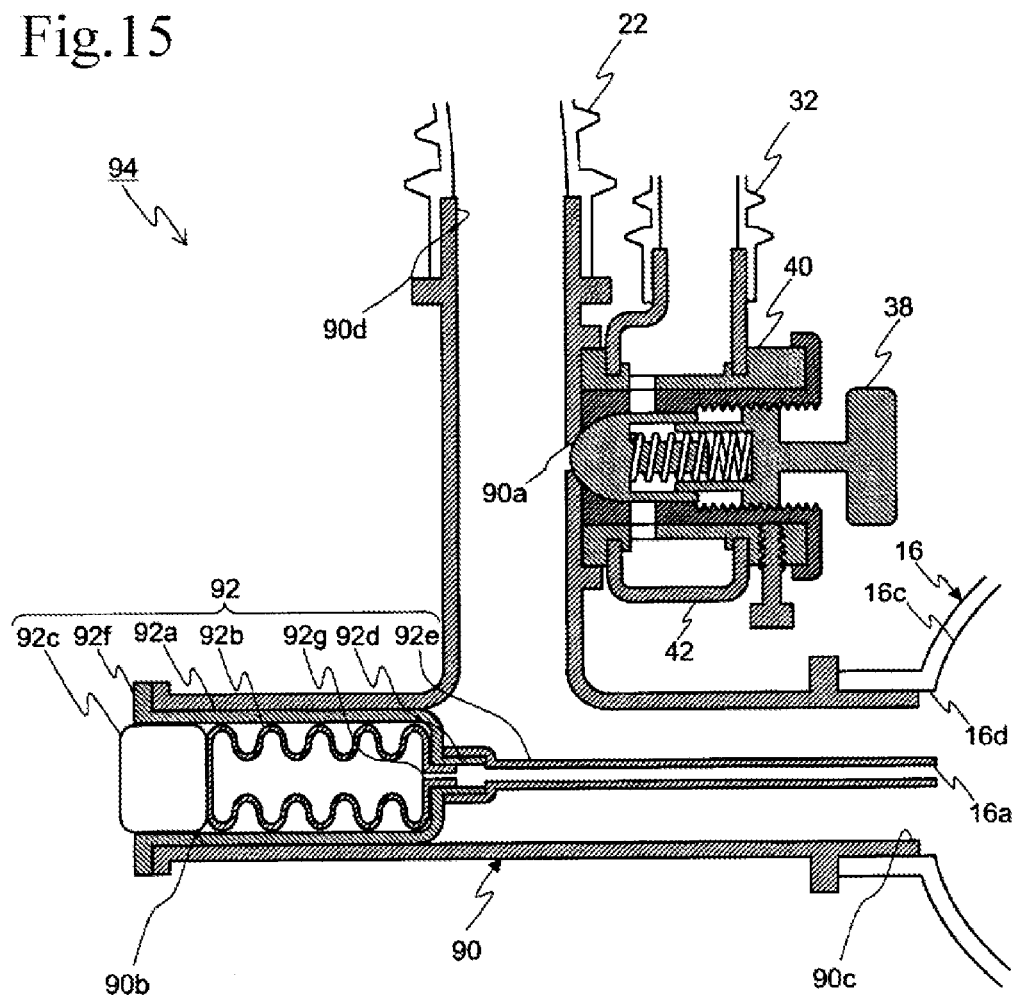
FIG. 15 is a partial cross-sectional view illustrating an anesthesia attachment of the fourth embodiment.

With reference to FIG. 15, the hollow structure 90 has four openings of a first opening 90a, second opening 90b, third opening 90c, and fourth opening 90d. The first opening 90a functions as an inlet of the valve in the relief valve 38 (the sleeve 40 and the exhaust camber 42 are provided to the relief valve 38 as in the first embodiment). The hollow structure 90 is connected to the Vapo-Ject 92 at the second opening 90b, connected to the elastic bag 16 at the third opening 90c through the outlet port 16a, and in communicative connection with the extension tube 32 at the fourth opening 90d. For example, the hollow structure 90 may be in the form of a T-shaped tubal structure brunched in three different directions. In such a hollow structure 90, the two openings in the opposite directions among the three openings may function as the second opening 90b and the third opening 90c, respectively, the other opening may function as the fourth opening 90d, and the first opening 90a may be formed so as to penetrate any tube wall. In view of the operability of the anesthetic inhalation aid device 88, it is preferred that the hollow structure 90 be configured so as to be rotatable around the axis of the extension tube 22. The relief valve 38 may be configured as other component than the hollow structure 90 so as to be detachably attached to the hollow structure 90.

Figure 16:
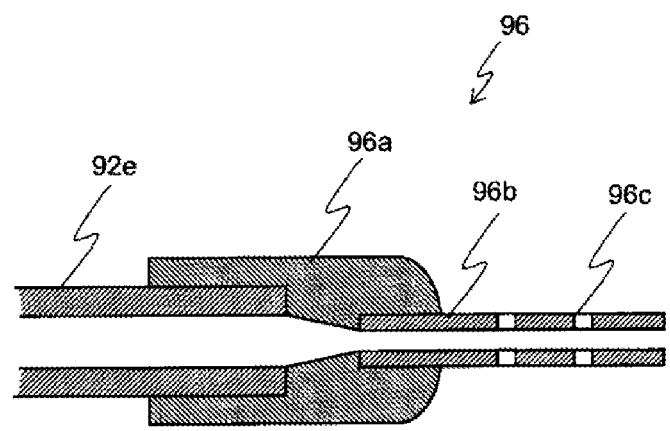
FIG. 16 is a cross-sectional view illustrating an injection needle attached to the tip of an extension nozzle.

The Vapo-Ject 92 functions as an anesthetic injector for injecting an anesthetic into the mixing chamber 16c of the elastic bag 16 and includes a bottomed cylindrical syringe 92a, a contractive bag 92b being a reservoir holding an anesthetic, a plunger 92c, a syringe nozzle 92d, and an extension nozzle 92e. The Vapo-Ject 92 is a component provided aside from the hollow structure 90. The syringe 92a tightly mates with the second opening 90b of the hollow structure 90. The syringe 92a is inserted into the second opening 90b until the flange 92f formed at its opening edge abuts on the hollow structure 90. The syringe 92a is formed so as not to disturb the flow of mixed gas from the mixing chamber 16c of the elastic bag 16 to the extension tube 22 through the third opening 90c and the fourth opening 90d as much as possible; for example, its length in the axial direction is adjusted. The contractive bag 92b is an elastic container, such as a bellows container, accommodated in the syringe 92a and has an anesthetic extraction port 92g for extracting the stored anesthetic, the anesthetic extraction port 92b is positioned at the bottom of the syringe 92a being in the accommodated state. The contractive bag 92b holds an anesthetic in an amount sufficient to make the patient 14 unconscious (e.g., approximately 5 milliliters) in a short time (e.g., approximately 10 to 30 minutes). The plunger 92c functions as a pump which moves inside the syringe 92a in the axial direction and compressively presses the contractive bag 92b against the bottom of the syringe 92a. The syringe nozzle 92d is formed as a communication channel between the interior and exterior of the syringe 92a so as to protrude from the bottom of the syringe 92a to the exterior thereof. Since the syringe nozzle 92a is in communicative connection with the contractive bag 92b through the anesthetic extraction port 92g, the contractive bag 92b is in communication with the exterior of the syringe 92a through the syringe nozzle 92d, so that the syringe 92a functions as a connector for the contractive bag 92b. The extension nozzle 92e is in communicative connection with the syringe nozzle 92d at the base end thereof, has a tubular structure having an end extending to the mixing chamber 16c of the elastic bag 16, and functions as an anesthetic extraction channel for unidirectionally introducing an anesthetic in the contractive bag 92b to the exterior. Such an end of the extension nozzle 92e can be connected to a commercially available injection needle 96, which has a needle base 96a and a needle tube 96b fixed thereto, through the needle base 96a as illustrated in FIG. 16. For instance, an injection needle having relatively small thickness of a 27G gauge is connected to form an atomizer which atomizes an anesthetic to be injected into the mixing chamber 16c to facilitate vaporization thereof. In contrast, for instance, in the case where an injection needle having relatively large thickness of a 18G gauge is connected, one or more pores 96c are formed in the needle tube 96b so as to penetrate a tube wall, so that the anesthetic is injected from the individual pores 96a into the mixing chamber 16c in a reduced amount to facilitate vaporization thereof. The tip of the extension nozzle 92e or the tip of the needle tube 96b of the injection needle 96 attached thereto functions as the anesthetic inlet 16a of the elastic bag 16.

In the Vapo-Ject 92 having such a configuration, the contractive bag 92b alone or a group of syringe 92a (including the syringe nozzle 92d and the flange 92f), contractive bag 92b, and a plunger 92c is provided in the form of a cartridge; in the case where an anesthetic in the contractive bag 92b runs short, the cartridge is changed to refill the anesthetic. Instead of this configuration, the contractive bag 92b may be filled with an anesthetic supplied from the anesthetic bottle 12 through the syringe nozzle 92d or the extension nozzle 92e.

Figure 17:
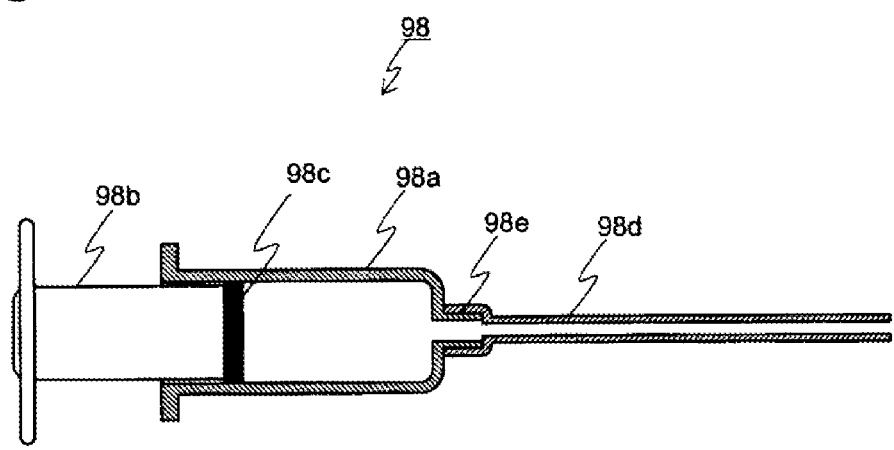
FIG. 17 is a partial cross-sectional view illustrating another example of a volatilization injector syringe.

As illustrated in FIG. 17, a Vapo-Ject 98 having some differences in the structure from the Vapo-Ject 92 may be used in the anesthesia attachment 94. In particular, the Vapo-Ject 98 is different from the Vapo-Ject 92 in the following: the contractive bag 92b is not used, an anesthetic is directly contained in a syringe 98a corresponding to the syringe 92a, a gasket 98c is attached to the tip of a plunger 98b corresponding to the plunger 92c to keep airtightness, and the plunger 98b directly applies pressure to the anesthetic. In such a Vapo-Ject 92, the syringe 98a functions not only as a reservoir holding an anesthetic but also as a connector for connecting the reservoir to the second opening 90b, and the syringe nozzle 98e functions not only as an anesthetic extraction port but also as a connector for attaching an extension nozzle 98d being an anesthetic extraction channel.

The operation of the anesthetic inhalation aid device 88 having such a configuration will now be described.

An anesthetic injected from the Vapo-Ject 92 or 98 into the mixing chamber 16c of the elastic bag 16 through the anesthetic inlet 16a is quickly vaporized into anesthetic gas, and the anesthetic gas is mixed with gas or air introduced from the air inlet 16b or the spare inlet 16e into mixed gas. The mixed gas is allowed to flow into the hollow structure 90 through the outlet port 16d of the elastic bag 16 by manual compression of the elastic bag 16 to transport compressed oxygen or compressed air from a pressure container trough the spare inlet 16e at a certain flow rate (e.g., 10 liters per minute) or by spontaneous respiration, and then the mixed gas passes through the extension tube 22, the anesthetic gas concentration detector 28, the artificial nose unit 20, and the inhalation mask 18 in sequence and is finally inhaled by the patient 14. The expired air of the patient 14 passes in the reverse sequence and then reaches the anesthesia attachment 94, and then the expired air opens the relief valve 38 in the case where the expiratory pressure is not less than a predetermined pressure P. Part of the expired air of the patient 14 passes through the relief valve 38, the sleeve 40, the exhaust chamber 42, the exhaust tube 32, and the anesthetic removal equipment 26 in sequence to remove the anesthetic and is then released to the atmosphere. The frequency of spraying an anesthetic with the Vapo-Ject 92 or 98 is appropriately determined through observation of the concentration of anesthetic gas shown by the display 30 which receives signals related to the concentration of the anesthetic gas from the anesthetic gas concentration detector 28.

In the anesthetic inhalation aid device 88 of the fourth embodiment, at least the Vapo-Ject 92 or 98 is provided separately from the hollow structure 90, and the Vapo-Ject 92 or 98 is connected to the hollow structure 90 to form the anesthesia attachment 94, which can simplify mold design and reduce production costs as compared with the anesthesia attachment 24 or the like into which the anesthetic extraction unit 44 is integrally incorporated.

In addition, the anesthetic inhalation aid device 88 eliminates direct injection into the body and involves use of the Vapo-Ject 92 or 98 for injection of an anesthetic into the elastic bag 16 to administer vaporized anesthetic gas to the body through respiration; in this regard, the anesthetic inhalation aid device 88 is a unique medical device which does not meet the definition of the traditional inhalation anesthesia devices. Such a Vapo-Ject 92 or 98 is less likely to cause excess administration as compared with any other administration technique, and even if a serious side effect is developed, drugs can be sequentially eliminated from the body only by stopping the injection of the drugs and continuing ventilation because inhalational anesthetics can be characteristically absorbed and exhausted through the lungs. Furthermore, the Vapo-Ject 92 or 98 is expected to be widely used as in general injectors.

Figure 18:
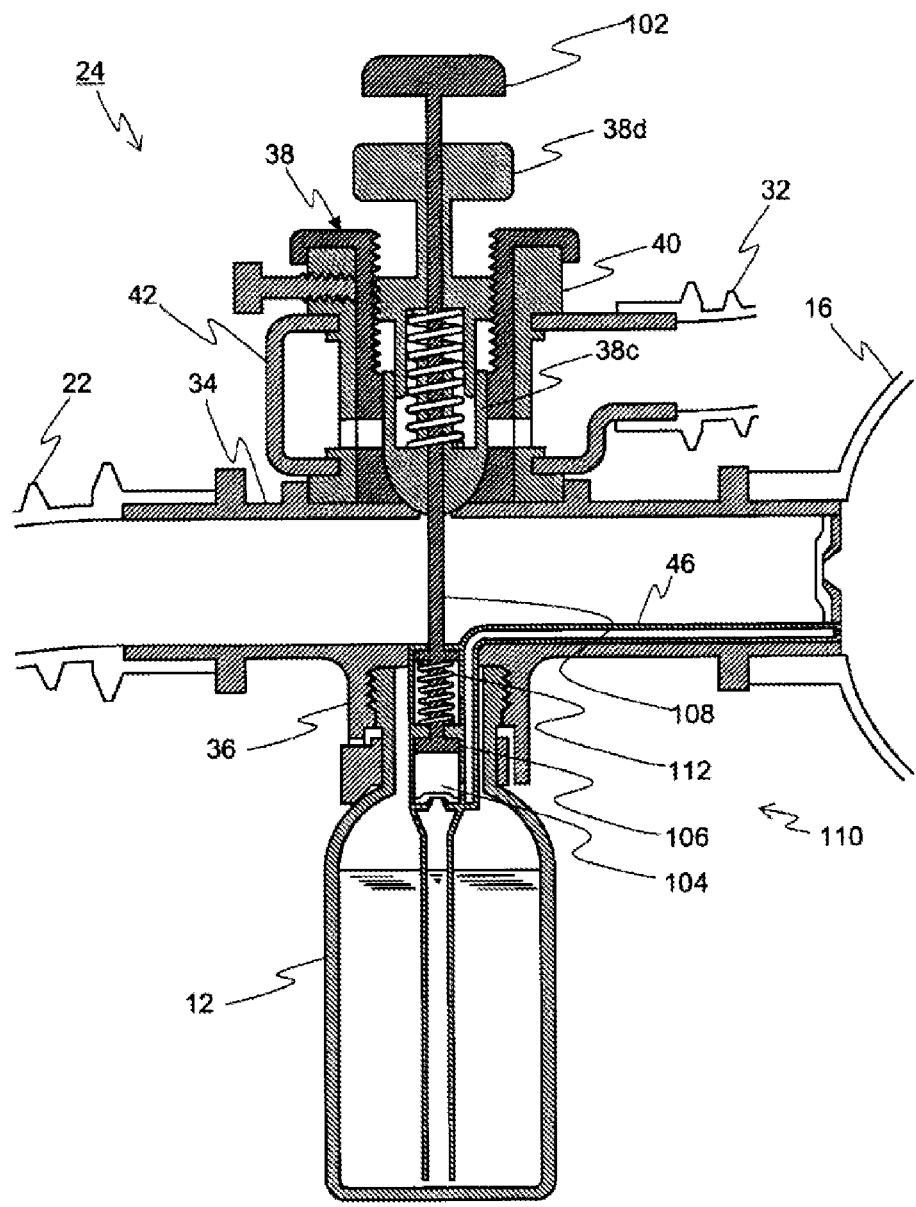
FIG. 18 illustrates another example of the anesthesia attachment provided with another pump.

In the anesthesia attachment 24 of the first embodiment, the mechanism in which an anesthetic held by the anesthetic bottle 12 is drawn and then pumped to the anesthetic inlet 16a of the elastic bag 16 through the anesthetic extraction tube 46 is not limited to the pump 52 operated with the lever 52b. For example, a pump 110 having a pump shaft 108 which has a pump head 102 formed at its base end and a plunger 106 formed at its tip may be provided as illustrated in FIG. 18, the pump shaft 108 extending from the base end to a cylinder 104 so as to slidably penetrate the handle 38d and the valve body 38c, the cylinder 104 being provided to the anesthetic extraction tube 46, and the plunger 106 being able to reciprocate in the cylinder 104. In the pump 110, the plunger 106 is reciprocated by a press of the pump head 102 in the direction of the tip and biasing force generated by a spring 112 urged in the direction of the base end, which can pump an anesthetic out of the anesthetic bottle 12 to the elastic bag 16 as in the pump 52 of the first embodiment operated with the lever 52b.

Figure 19:
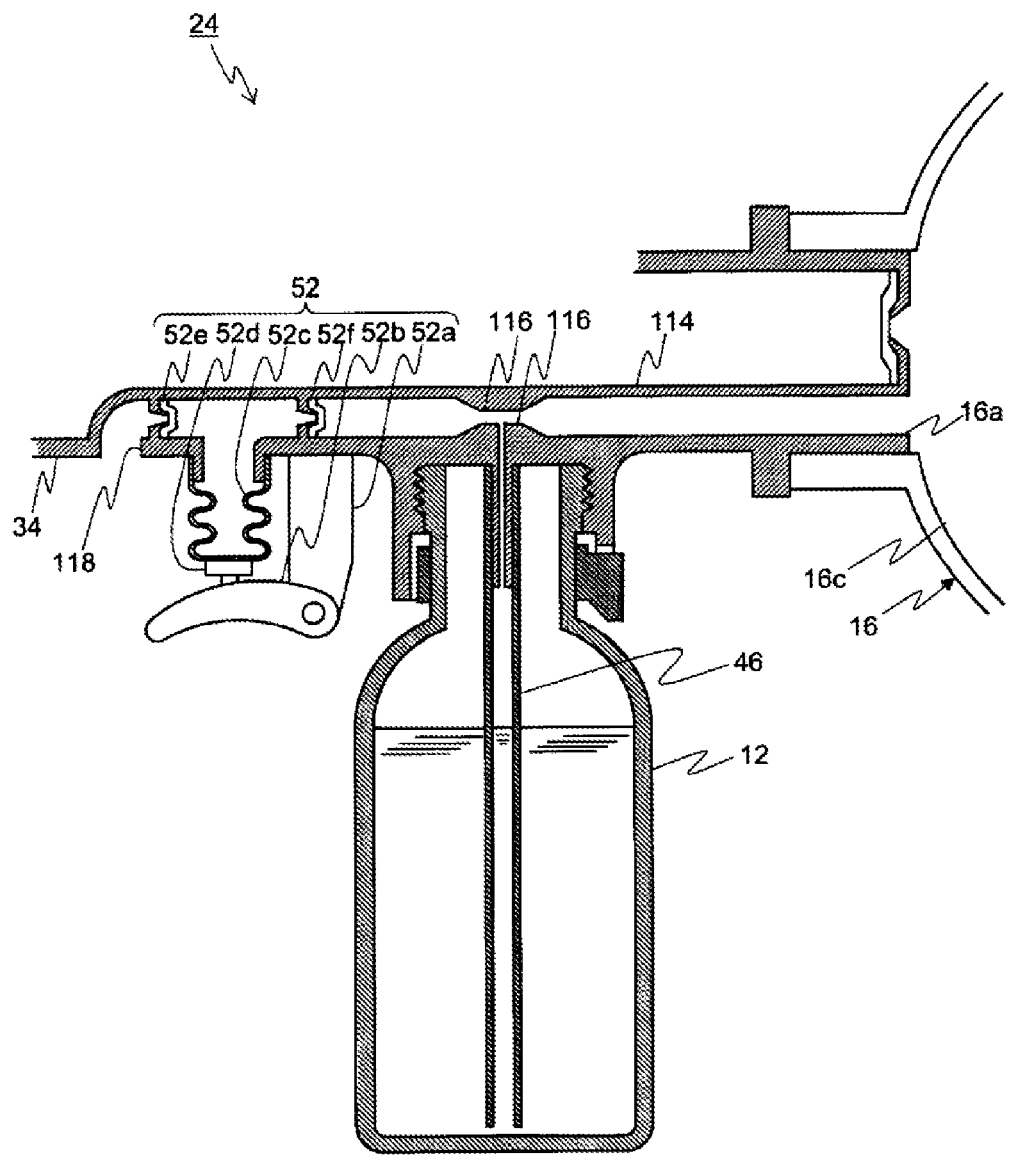
FIG. 19 is a partial cross-sectional view illustrating an example of an atomizer utilizing a spraying mechanism.

In the anesthesia attachment 24 of the first embodiment, the mechanism for atomizing an anesthetic is not limited to the nozzle 54; in place thereof, an atomizer employing the mechanism of a spray gun may be provided. In an exemplary structure illustrated in FIG. 19, an air pumping tube 114 is provided to pump air out of the pump 52 to the mixing chamber 16c of the elastic bag 16, a narrow portion 116 is provided to the interior of the air pumping tube 114 to narrow the channel, and the narrow portion 116 is in communication with the internal of the anesthetic bottle 12 through the anesthetic extraction tube 46. In this structure, the pump 52 has the supporting frame 52a, the lever 52b, the bellows cylinder 52c, the connection rod 52d, the inflow valve 52e, and the outflow valve 52f. The hollow structure 34 has a continuous hole 118 which forms a communication between the interior of the bellows cylinder 52c and ambient air when the inflow valve 52e opens.

In such an atomizer utilizing the mechanism of a spray gun, ambient air is introduced into the interior of the bellows cylinder 52c through the continuous hole 118 and the outflow valve 52e while the contracted bellows cylinder 52a expands into the original state by its own elastic force. During this process, since the outflow valve 52f is opened by the unidirectional flow from the bellows cylinder 52a to the anesthetic inlet 16a, the interior of the bellows cylinder 52a is free from the intrusion of gas from the mixing chamber 16c of the mixing bag 16 and the intrusion of the anesthetic from the anesthetic bottle 12. In contrast, the air introduced into the interior of the bellows cylinder 52a opens the outflow valve 52f and then is pumped to the anesthetic inlet 16a while the bellows cylinder 52a is contracted, which does not open the outflow valve 52e which is opened by unidirectional flow from the continuous hole 118 to the bellows cylinder 52c.

In the atomizer utilizing the mechanism of a spray gun, since air pumped out of the pump 52 generates the Venturi effect at the narrow portion 116, an anesthetic in the anesthetic bottle 12 is drawn to the narrow portion 116 through the anesthetic extraction tube 46 owing to generation of negative pressure and then is atomized owing to an air jet. The atomized anesthetic flows together with pumped air through part of the air pumping tube 114 between the narrow portion 16 and the anesthetic inlet 16a, and such part of the air pumping tube 114 therefore also functions as the anesthetic extraction tube 46. Furthermore, the actuator of the second embodiment can be used instead of the manual lever 52b of the pump 52 to automatically control the concentration of an anesthetic even in the case where the anesthetic is sprayed with the atomizer utilizing the mechanism of a spray gun.

In the anesthesia attachment 24 of the first embodiment, the anesthetic extraction unit 44 may not include the pump 52. In particular, negative pressure generated in the mixing chamber 16c during the elastic expansion of the contracted elastic bag 16 into the original state may be utilized to pump an anesthetic out of the anesthetic bottle 12 to the mixing chamber 16c. Such a configuration eliminates use of the pump 52, which can further reduce the weight of the anesthetic inhalation aid device 10 or 88. In this case, the inflow valve 52e or the outflow valve 52f is preferably provided to prevent the flow of gas in the mixing chamber 16c into the anesthetic bottle 12 through the anesthetic extraction tube 46 during the contraction of the elastic bag 16.

In each of the first, second, and fourth embodiments, the anesthetic bottle 12 may be a container which contracts with a reduction in the volume of an anesthetic contained therein. For instance, in the anesthetic bottle 12, the cylinder portion, at which the anesthetic outlet 12a and the screw thread 12b are formed, may be formed so as to be less likely to be deformed, and the body in which an anesthetic is contained may be composed of readily deformable and flexible material. The body may be, for example, a metal tube formed from an aluminum thin film or a laminated tube formed by laminating synthetic resin or an aluminum thin film. An anesthetic in the anesthetic bottle 12 having such a configuration is drawn with the pump 52, which can flexibly deform the body of the anesthetic bottle 12 due to the contraction in response to the amount of the taken anesthetic. In addition, since the inflow valve 52e and outflow valve 52f of the pump 52 prevent gas in the mixing chamber 16c from flowing into the anesthetic bottle 12, the deformation of the body caused by drawing the anesthetic can be readily maintained, which prevents the expansion of the body. This prevents a status in which the anesthetic is not at the inlet of the anesthetic extraction tube 46 in the anesthetic bottle 12, so that the anesthetic can be steadily drawn from the anesthetic bottle 12 and then sprayed with the pump 52 even in the case where the anesthetic inhalation aid device 10 is used in weightless environments.

Figure 20:
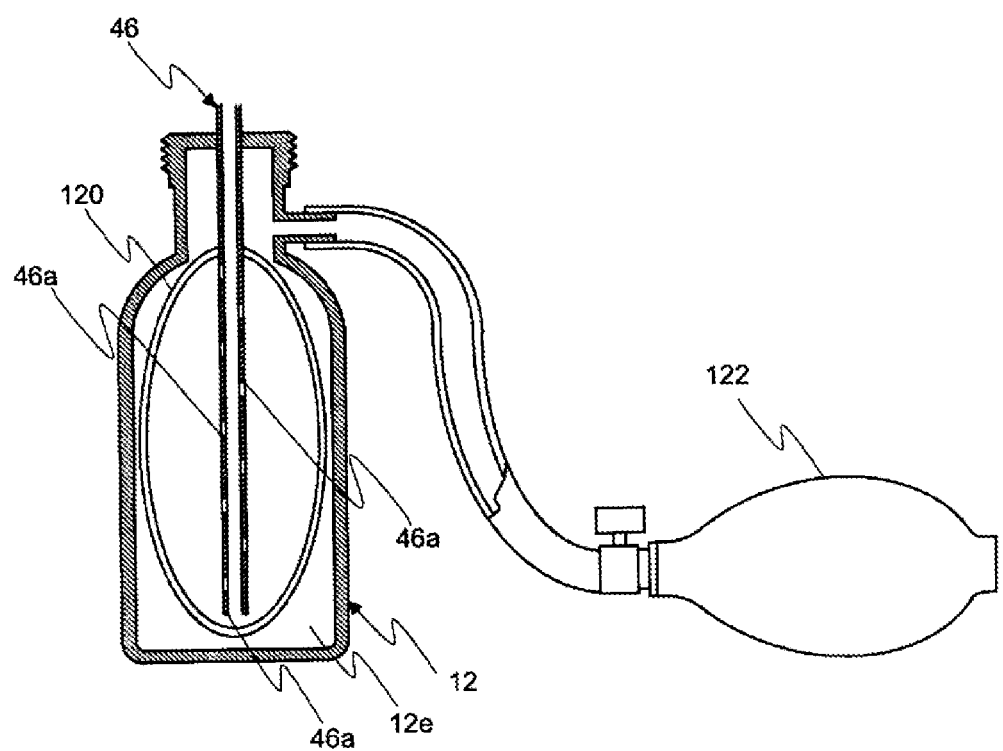
FIG. 20 is a partial cross-sectional view illustrating an example of application of pressure to an anesthetic bag accommodated in the anesthetic bottle.

In each of the first, second, and fourth embodiments, the anesthetic bottle 12 may not directly hold an anesthetic and may accommodate another container which holds the anesthetic and contracts as the volume of the anesthetic is reduced. For example, an anesthetic bag 120 being a deformable airtight bag for holding an anesthetic is accommodated in the anesthetic bottle 12 as illustrated in FIG. 20. An anesthetic extraction tube 46 is inserted into the anesthetic bag 120 such that an anesthetic inlet 46a is positioned inside the anesthetic bag 120. An external pressure source 122 (e.g., squeeze bulb) is attached to the anesthetic bottle 12 to apply a pressure to enclosed inner space 12e of the anesthetic bottle 12 and maintain the pressurized state. In this structure, applying pressure to the inner space 12e of the anesthetic bottle 12 with the external pressure source 122 causes the anesthetic bag 120 to be contracted, so that gas remaining inside the anesthetic bag 120 is exhausted to the exterior of the anesthetic bag 120 through the anesthetic extraction tube 46. Hence, the anesthetic can be also steadily drawn from the anesthetic bottle 12 and then sprayed with the pump 52 even in the case where the anesthetic inhalation aid device 10 is used in weightless environments. It is preferred that multiple inlets 46a be formed in the anesthetic extraction tube 46 to steadily draw an anesthetic from the anesthetic bottle 12.

In the anesthetic inhalation aid device 10 of the first to third embodiments, each of the anesthesia attachments 24, 56, and 70 may be provided between the extension tube 22 and the artificial unit 20 or between the artificial unit 20 and the inhalation mask 18, instead of being provided between the elastic bag 16 and the extension tube 22. In the anesthetic inhalation aid device 88 of the fourth embodiment, the hollow structure 90 may be directly in communicative connection with the branched tube 28 without being connected to the extension tube 22.

In each of the anesthetic inhalation aid devices 10 and 88 of the first to fourth embodiments, the mixed gas inlet valve 34d, the inflow valve 52e, the outflow valve 52f, and the anesthetic check valve 86 are not limited to the structure in which a rubber on-off valve is provided to a through-hole narrowing a channel. Well-known check valves, such as a flap valve, may be employed, in which a valve body is pressed by a fluid into an opened state, whereas a back pressure generated by a backflow causes the valve body to be tightly seated on a valve seat in a channel to stop the flow.

The entire contents of Japanese Patent Application No. 2011-122801 filed in the Japan Patent Office on May 31, 2011 are incorporated herein by reference on the basis of its claiming priority.

The embodiments have been given only to illustrate and describe the present invention, and the present invention can be variously changed and modified without departing from the scope of the present invention as is defined by the scope of appended CLAIMS, which will be understood by the person skilled in the art.

The description of the embodiments of the present invention has been made only to exemplify the present invention, and the present invention (invention claimed in appended CLAIMS or invention equivalent thereto) should not be limited thereto.

REFERENCE SIGNS LIST

10 . . . anesthetic inhalation aid device, 12 . . . anesthetic bottle, 14 . . . patient, 16 . . . elastic bag, 16a . . . anesthetic inlet, 16b . . . air inlet, 16c, mixing chamber, 16d . . . outlet port, 16e . . . spare inlet, 18 . . . inhalation mask, 20 . . . artificial nose unit, 22 . . . extension tube, 24, 56, 70, and 94 . . . anesthesia attachment, 26 . . . anesthetic removal equipment, 28 . . . anesthetic gas concentration detector, 30 . . . display, 32 . . . exhaust tube, 34 and 90 . . . hollow structure, 36 . . . connector, 38 . . . relief valve, 40 . . . sleeve, 42 . . . exhaust chamber, 44 and 72 . . . anesthetic extraction unit, 46 . . . anesthetic extraction tube, 52 and 58 . . . pump, 54 . . . nozzle, 60 . . . anesthetic gas concentration control unit, 62 . . . driver, 68 . . . control part, 74 . . . expired air introduction tube, 92 and 98 . . . vaporization injector syringe

The invention claimed is:

1. An anesthetic inhalation aid device used for inhalation administration of an anesthetic in a reservoir to a patient, the anesthetic inhalation aid device comprising:
    a connector that is detachably and airtightly connectable to an anesthetic outlet of the reservoir;
    an anesthetic extraction unit connected to the connector, being in communication with the interior of the reservoir, and including an anesthetic extraction channel for unidirectionally introducing the anesthetic from the interior of the reservoir to the exterior;

a mixer having an anesthetic inlet for introducing the anesthetic inward through the anesthetic extraction channel, an oxygen-containing gas inlet for unidirectionally introducing oxygen-containing gas at least containing oxygen from the exterior to the interior, a mixing chamber for mixing the introduced anesthetic with the oxygen-containing gas, and an outlet port for exhausting the mixed gas generated in the mixing chamber outward from the mixing chamber, the anesthetic inlet being formed so as to extend from the outlet port to the mixing chamber;

a mixed gas introduction passage for unidirectionally introducing the mixed gas from the outlet port to the oral cavity or nasal cavity of the patient;

a relief valve that opens when the internal pressure of the mixed gas introduction passage reaches a level greater than or equal to a first predetermined pressure; and a remover that removes an anesthetic content in gas exhausted from the relief valve, wherein the mixer is configured as an elastic bag that is elastically deformed by hand to increase and decrease the volume of the mixing chamber, the mixed gas is exhausted from the outlet port when the volume is decreased, and the oxygen-containing gas is introduced from the oxygen-containing gas inlet when the volume is increased.

2. The anesthetic inhalation aid device according to claim 1, wherein the anesthetic extraction unit further includes a pump that serves to pump out the anesthetic in the reservoir to the anesthetic inlet through the anesthetic extraction channel.

3. The anesthetic inhalation aid device according to claim 2, wherein the anesthetic extraction unit further includes an atomizer provided to the anesthetic extraction channel to atomize the anesthetic pumped out with the pump.

4. The anesthetic inhalation aid device according to claim 2, further comprising:
an anesthetic gas concentration detector that detects the concentration of anesthetic gas in the mixed gas introduction passage; and
a display that shows the concentration of the anesthetic gas detected by the anesthetic gas concentration detector.

5. The anesthetic inhalation aid device according to claim 4, further comprising:
an actuator configured so as to operate the pump;
a driving circuit configured so as to drive the actuator; and
a control circuit that controls the driving circuit such that the detection concentration detected by the anesthetic gas concentration detector automatically approaches a target concentration determined depending on a symptom of the patient.

6. The anesthetic inhalation aid device according to claim 1, wherein the anesthetic extraction unit further includes a pump that serves to pump air to the anesthetic inlet, wherein
the anesthetic in the reservoir is drawn through the anesthetic extraction channel and then atomized owing to the jet flow of air pumped from the pump to the anesthetic inlet, and the atomized anesthetic is introduced into the anesthetic inlet together with the pumped air.

7. The anesthetic inhalation aid device according to claim 1, wherein the anesthetic extraction unit includes a heater that heats an anesthetic flowing in the anesthetic extraction channel.

8. The anesthetic inhalation aid device according to claim 1, wherein the anesthetic extraction unit further includes an expired air introduction passage that unidirectionally introduces the expired air of the patient into the inner space of the reservoir, wherein the anesthetic extraction channel introduces the anesthetic in the reservoir into the anesthetic inlet of the mixer by the pressure of the introduced expired air.

9. The anesthetic inhalation aid device according to claim 1, wherein the reservoir is configured so as to be contracted as the volume of the anesthetic held by the reservoir is reduced.

10. The anesthetic inhalation aid device according to claim 1, further comprising an exhaust adjuster that continuously changes the closed state of an exhaust port of the relief valve to adjust the amount of exhaust air.

11. An attachment used in the anesthetic inhalation aid device according to claim 1, the attachment comprising:
the connector;
the anesthetic extraction unit;
at least part of the mixed gas introduction passage; and
the relief valve.

12. The attachment according to claim 11, wherein the mixed gas introduction passage includes
a first mixed gas introduction passage having an end detachably connected to the outlet port of the mixer, and
a second mixed gas introduction passage detachably connected to the other end of the first mixed gas introduction passage, wherein
at least part of the mixed gas introduction passage functions as the first mixed gas introduction passage.

13. The attachment according to claim 12, wherein the connector and the anesthetic extraction unit are provided as an integral unit that functions is an anesthetic injector.

14. The attachment according to claim 13, wherein the first mixed gas introduction passage has a hollow structure having a first opening that functions as a fluid inlet of the relief valve, a second opening connected to the anesthetic injector, a third opening that is in communicative connection with the mixer through the outlet port, and a fourth opening that is in communicative connection with the second mixed gas introduction passage.

15. The attachment according to claim 14, wherein the anesthetic injector is detachably connected to the second opening.

16. The attachment according to claim 15, wherein the hollow structure is a substantially T-shaped tubal structure, and the two openings in the opposite directions among the three openings function as the second opening and the third opening, respectively.

17. The attachment according to claim 16, wherein the anesthetic injector includes an injection needle.

18. The attachment according to claim 17, wherein the second mixed gas introduction passage includes an inhalation mask that covers the oral cavity and nasal cavity of the patient to enable the patient to inhale the mixed gas and an artificial nose unit that holds heat and moisture derived from the expired air of the patient.

19. The attachment according to claim 12, wherein the connector, the anesthetic extraction unit, and the first mixed gas introduction passage are provided as an integral unit.

20. The attachment according to claim 19, wherein the relief valve is provided to the first mixed gas introduction passage.

21. The attachment according to claim 14, wherein the valve-opening area of the relief valve in the first opening is determined such that the relief valve is closed when the internal pressure of the mixed gas introduction passage is reduced to a second predetermined pressure lower than the first predetermined pressure after the relief valve is opened.

* * * * *